United States Patent
Cuervo et al.

(10) Patent No.: US 8,618,042 B2
(45) Date of Patent: Dec. 31, 2013

(54) BINDING MOLECULES AND METHODS OF USE THEREOF

(75) Inventors: Julio H. Cuervo, Arlington, MA (US); Russell C. Petter, Stow, MA (US); Daniel Scott, Weston, MA (US); Kathryn Strauch, Bedford, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 1087 days.

(21) Appl. No.: 11/698,299

(22) Filed: Jan. 25, 2007

(65) Prior Publication Data

US 2007/0248988 A1 Oct. 25, 2007

Related U.S. Application Data

(63) Continuation of application No. PCT/US2005/027262, filed on Aug. 1, 2005.

(60) Provisional application No. 60/592,886, filed on Jul. 30, 2004, provisional application No. 60/592,787, filed on Jul. 30, 2004.

(51) Int. Cl.
*A01N 61/00* (2006.01)

(52) U.S. Cl.
USPC ............................................................ 514/1

(58) Field of Classification Search
None
See application file for complete search history.

(56) References Cited

U.S. PATENT DOCUMENTS 5,824,805 A    10/1998    King et al.

FOREIGN PATENT DOCUMENTS

WO    WO 03/041642 A2 *    5/2003

OTHER PUBLICATIONS

Baselga et al (Cancer Research, Jul. 1998, 58(13): 2825-2831).*
Dubowchik, Gene M. et al., "Doxorubioin Immunoconjugates Containing Bivalent, Lysosomally-Cleavable Dipeptide Linkages," Bioorganic & Medicinal Chemistry Letters, vol. 12:1529-1532 (2002).
King, H. Dalton et al., "Monoclonal Antibody Conjugates of Doxorubicin Prepared with Branched Linkers: A Novel Method for Increasing the Potency of Doxorubicin Immunoconjugates," Bioconjugate Chem., vol. 10:279-288 (1999).
King, H. Dalton et al., "Monoclonal Antibody Conjugates of Doxorubicin Prepared with Branched Peptide Linkers: Inhibition of Aggregation by Methoxytriethyleneglycol Chains," J. Med. Chem., vol. 45:4336-4343 (2002).
Shih, Lisa B. et al., "Anthracycline Immunoconjugates Prepared by a Site-specific Linkage via an Amino-Dextran Intermediate Carrier," Cancer Research, vol. 51:4192-4198 (1991).
Trauger, John W. et al., "Cyclization of Backbone-Substituted Peptides Catalyzed by the Thioesterase Domain from the Tyrocidine Nonribosomal Peptide Synthetase," Biochemistry, vol. 40:7092-7098 (2001).
International Search Report Application No. PCT/US2005/027262, 10 pages, dated Mar. 14, 2007.
International Preliminary Report on Patentability and Written Opinion for Application No. PCT/US2005/027262, 17 pages, dated Mar. 27, 2007.

* cited by examiner

*Primary Examiner* — Sean Aeder
(74) *Attorney, Agent, or Firm* — Nelson Mullins Riley & Scarborough LLP; Debra J. Milasincic, Esq.

(57) ABSTRACT

Binding molecules are described.

68 Claims, No Drawings

BINDING MOLECULES AND METHODS OF USE THEREOF

RELATED APPLICATIONS

This application is a continuation of PCT/US2005/027262, filed Aug. 1, 2005; which claims priority to U.S. Provisional Application Ser. Nos. 60/592,886 and 60/592,787, both filed on Jul. 30, 2004, the entire contents of all of which are hereby incorporated herein by reference in their entirety.

BACKGROUND OF THE INVENTION

Methods of attaching drug moieties to binding molecules to facilitate targeting of drug moieties to specific cells or molecules are known in the art. However, using the prior art methods limits the number of drug moieties that are attached to each binding molecule. In addition, the prior art methods are limited in that they often result in attachment of drug moieties to sites that interfere with the ability of a binding molecule to bind to its target. The development of novel methods for linking drug or labeling moieties to binding molecules would be of great benefit.

SUMMARY OF THE INVENTION

The invention is based, at least in part, on the discovery of novel methods of linking drug, tag, and affinity labels to polypeptides comprising at least one binding site. This allows, for example, greater efficiency in administering cytotoxic agents to a subject. By attaching drug and other moieties to a binding molecule, when the binding molecule binds to its target the drug moieties are delivered to a specific cell or site.

In one embodiment, the invention pertains, at least in part to a binding molecule of the formula (I):

Ab-(M-Z$_r$)$_p$     (I)

wherein:
Ab is a polypeptide comprising at least one antigen binding site;
M is an independently selected branching moiety for each occurence;
Z is an independently selected drug moiety, affinity moiety, tag moiety, pharmacokinetic moiety, or Ab for each occurrence;
r is an integer greater than or equal to 2; and
p is an integer greater than or equal to 1, and pharmaceutically acceptable salts, esters, and prodrugs thereof, wherein Ab is linked to each M at a predetermined site on Ab.

In another embodiment, the invention pertains to a binding molecule of the formula (II):

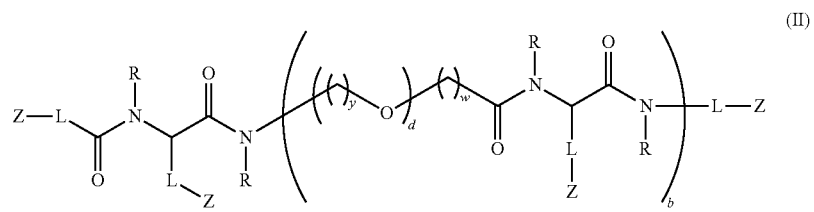

wherein
Ab is a polypeptide comprising at least one antigen binding site;
L is an independently selected linker moiety for each occurrence or B when Z is Ab;
B is a bridging moiety;
R is selected independently for each occurrence from the group consisting of alkyl, alkenyl, alkynyl, acyl, and hydrogen;
Z is an independently selected drug moiety, affinity moiety, tag moiety, hydrogen, amino acid side chain moiety, or Ab for each occurrence;
w and y are each independently selected for each occurrence from the group consisting of 1, 2, 3, 4, and 5;
b and d are each independently selected for each occurrence from integers greater than 1, provided that at least one Z is Ab, and pharmaceutically acceptable salts, esters, and prodrugs thereof.

In yet another embodiment, the invention pertains to a bridging composition of the formula (III):

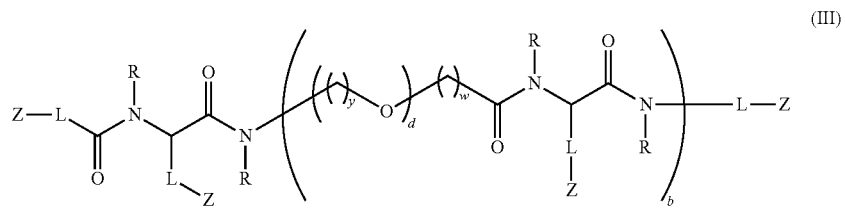

wherein

L is an independently selected linker moiety for each occurrence or B when Z is an attachment moiety;

B is a bridging moiety;

R is selected independently for each occurrence from the group consisting of alkyl, alkenyl, alkynyl, acyl, and hydrogen;

Z is an independently selected drug moiety, affinity moiety, tag moiety, hydrogen, amino acid side chain moiety, or an attachment moiety for each occurrence;

w and y are each independently selected for each occurrence from the group consisting of 1, 2, 3, 4, and 5;

b and d are each independently selected for each occurrence from integers greater than 1, provided that at least one Z is an attachment moiety, and pharmaceutically acceptable salts, esters, and prodrugs thereof.

In yet another embodiment, the invention pertains to methods for treating a subject suffering from a disorder that would benefit from treatment with a binding molecule, by administering to the subject an effective amount of a binding molecule of the invention.

In another embodiment, the invention pertains, at least in part but not limited to, to a method of treating a subject for cancer, by administering to the subject an effective amount of a binding molecule of the invention.

In another embodiment, the invention pertains, at least in part but not limited to, to a method of treating a subject for colorectal cancer, by administering to the subject an effective amount of a binding molecule of the invention.

In another embodiment, the invention pertains, at least in part but not limited to, to a method of treating a subject for pancreatic cancer, by administering to the subject an effective amount of a binding molecule of the invention.

In yet another embodiment, the invention also includes, for example, a method of treating a subject for acute myelogenous leukemia (AML), by administering to the subject an effective amount of a binding molecule of the invention.

The invention also pertains, at least in part, to a composition comprising a binding molecule of the invention and a pharmaceutically acceptable carrier.

In another embodiment, the invention also pertains to a method for the selective removal of a binding molecule from a mixture. The method includes contacting the mixture and the binding molecule of the invention with an affinity matrix, wherein at least one Z of the binding molecule is an affinity moiety with affinity for the affinity matrix.

In yet another embodiment, the invention also includes a method for imaging a target-expressing cell, e.g., a cell expressing a particular receptor, ligand, or antigen bound by the binding molecule. The method comprises contacting the cell with a binding molecule of the invention, wherein the binding molecule binds to a target on a cell or tissue and wherein at least one Z group is a tag moiety.

DETAILED DESCRIPTION OF THE INVENTION

Definitions

In order that the present invention may be more readily understood, certain terms are first defined. Additional definitions are set forth throughout the detailed description.

The binding molecules of the invention comprise a polypeptide which includes at least one binding site which specifically binds to a target molecule (such as an antigen or binding partner). For example, in one embodiment, a binding molecule of the invention comprises an immunoglobulin antigen binding site or the portion of a receptor molecule responsible for ligand binding or the portion of a ligand responsible for receptor binding.

The binding molecules of the invention may comprise at least one immunoglobulin domain. It will be understood by one of ordinary skill in the art that these domains (e.g., the heavy chain or light chain portions or other portions of the subject polypeptides that are derived from immunoglobulin molecules) may be modified such that they vary in amino acid sequence from the naturally occurring immunoglobulin molecule, without altering the desired antigen-binding ability of the resulting polypeptide. For example, nucleotide substitutions leading to amino acid substitutions at "non-essential" amino acid residues may be made.

An isolated nucleic acid molecule encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the immunoglobulin coding sequence, such as by saturation mutagenesis, and the resultant mutants can be incorporated into polypeptides of the invention and screened for their ability to bind to the desired antigen.

In one embodiment, the polypeptide comprising at least one binding site of the invention are "antibody" or "immunoglobulin" molecules, e.g., naturally occurring antibody or immunoglobulin molecules or genetically engineered binding molecules that comprise at least one antigen binding site. As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. a tumor associated antigen). Antibodies and immunoglobulins comprise light and heavy chains, with or without an interchain covalent linkage between them. Basic immunoglobulin structures in vertebrate systems are relatively well understood.

As will be discussed in more detail below, the generic term "immunoglobulin" comprises five distinct classes of antibody that can be distinguished biochemically. All five classes of antibodies are clearly within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively.

Light chains are classified as either kappa or lambda ($\kappa, \lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunogobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, ($\gamma, \mu, \alpha, \delta, \epsilon$) with some subclasses among them (e.g., $\gamma_1$-$\gamma 4$). It is the nature of this chain that determines the "class" of the antibody as IgG, IgM, IgA IgG, or IgE, respectively. The immunoglobulin subclasses (isotypes) e.g., $IgG_1, IgG_2, IgG_3, IgG_4, IgA_1$, etc. are well characterized and are known to confer functional specialization. Modified versions of each of these classes and isotypes are readily discernable to the skilled artisan in view of the instant disclosure and, accordingly, are within the scope of the instant invention.

As indicated above, the variable region allows the antibody to selectively recognize and specifically bind epitopes on antigens. That is, the $V_L$ domain and $V_H$ domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the $V_H$ and $V_L$ chains. As used herein, the term "antigen binding site" includes the site that specifically binds with an antigen. An antigen binding site is formed by variable regions that vary from one polypeptide to another. The polypeptides comprising two heavy chain portions disclosed herein may be linked to form two associated Ys so there will be four binding sites forming a "tetravalent" molecule (see e.g., WO02/096948A2)). In another embodiment, tetravalent minibodies or domain deleted antibodies can be made.

As used herein the term "valency" refers to the number of potential target binding sites in a polypeptide. Each target binding site specifically binds one target molecule. When a polypeptide comprises more than one target binding site, each target binding site may specifically bind the same or different molecules (e.g. may bind to different ligands or different antigens, or different epitopes on the same antigen).

The term "specificity" includes the number of potential target binding sites which immunoreact with (specifically bind) a given target. A polypeptide may be monospecific and contain one or more target binding sites which specifically bind an target or a polypeptide may be bispecific and contain two or more target binding sites which specifically bind the same or different molecules.

In still another embodiment, bispecific molecules (e.g., antibodies, minibodies, domain deleted antibodies, or fusion proteins) having binding specificity for more than one molecule, e.g., more than one antigen or more than one epitope on the same antigen can be made.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope.

The polypeptides of the instant invention may comprise at least two binding sites that provide for the association of the polypeptide with the selected target. In one embodiment, the at least two binding sites are antigen binding sites. In this regard, the variable region may or be derived from any type of animal that can be induced to mount a humoral response and generate immunoglobulins against the desired antigen. As such, the variable region of the polypeptides may be, for example, of mammalian origin e.g., may be human, murine, non-human primate (such as cynomolgus monkeys, macaques, etc.), lupine, camelid (e.g., from camels, llamas and related species). In another embodiment, the variable region may be condricthoid in origin (e.g., from sharks).

Binding molecules, e.g., antigen binding molecules can be made using techniques that are known in the art. In one embodiment, the polypeptides of the invention comprising at least one antigen binding site are antibody molecules that have been "recombinantly produced." Exemplary techniques for making antibody molecules are discussed in more detail below.

In one embodiment, the polypeptides of the invention comprising at least one antigen binding site are modified antibodies. As used herein, the term "modified antibody" includes altered forms of antibodies which are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen) and antigen-binding fusion proteins, e.g., fusion proteins comprising at least one heavy chain portion and comprising a binding domain of a polypeptide).

In one embodiment, the term, "modified antibody" according to the present invention includes immunoglobulins, antibodies, or immunoreactive fragments or recombinants thereof, in which at least a fraction of one or more of the constant region domains has been deleted or otherwise altered so as to provide desired biochemical characteristics such as the ability to non-covalently dimerize, increased ability to localize at the site of a tumor, or reduced serum half-life when compared with a whole, unaltered antibody of approximately the same immunogenicity. In a preferred embodiment, the polypeptides of the present invention are domain deleted antibodies which comprise a polypeptide chain similar to an immunoglobulin heavy chain, but which lack at least a portion of one or more heavy chain domains. More preferably, one entire domain of the constant region of the modified antibody will be deleted and even more preferably the entire CH2 domain will be deleted.

In preferred embodiments, the binding molecule of the invention will not elicit a deleterious immune response in a human. Modifications to the constant region compatible with the instant invention comprise additions, deletions or substitutions of one or more amino acids in one or more domains. That is, the binding molecules of the invention disclosed herein may comprise alterations or modifications to one or more of the three heavy chain constant domains (CH1, CH2 or CH3) and/or to the light chain constant region domain (CL).

In one embodiment, the binding molecules of the invention may be modified to reduce their immunogenicity using art-recognized techniques. For example, the polypeptide portions of the antigen binding molecules of the invention of the invention can be humanized, deimmunized, or chimeric antibodies can be made. These types of antibodies are derived from a non-human antibody, typically a murine antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81: 6851-5 (1984); Morrison et al, *Adv. Immunol.* 44: 65-92 (1988); Verhoeyen et al., *Science* 239: 1534-1536 (1988); Padlan, *Molec. Immun.* 28: 489-498 (1991); Padlan, *Molec. Immun.* 31: 169-217 (1994), and U.S. Pat. Nos. 5,585,089, 5,693,761 and 5,693,762 all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of polypeptides of the invention that are tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Those skilled in the art will appreciate that chimeric antibodies can also be used as the polypeptide comprising at least one antigen binding site of the invention. In the context of the present application the term "chimeric antibodies" will be held to mean any antibody wherein the immunoreactive region or site is obtained or derived from a first species and the constant region (which may be intact, partial or modified in accordance with the instant invention) is obtained from a second species. In preferred embodiments the antigen binding region or site will be from a non-human source (e.g. mouse) and the constant region is human. While the immunogenic specificity of the variable region is not generally affected by its source, a human constant region is less likely to elicit an immune response from a human subject than would the constant region from a non-human source.

Preferably, the variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

In another embodiment, the polypeptides comprising at least one binding site described herein may be altered to provide for altered effector functionality that, e.g., affects the biological profile of the administered antigen binding molecule. For example, the deletion or inactivation (through point mutations or other means) of a constant region domain may reduce Fc receptor binding of the circulating antigen binding molecule thereby increasing tumor localization. In other cases it may be that constant region modifications consistent with the instant invention moderate compliment binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. More generally, those skilled in the art will realize that the binding molecules as described herein may exert a number of subtle effects that may or may not be readily appreciated. However the resulting physiological profile, bioavailability and other biochemical effects of the modifications, such as tumor localization and serum half-life, may easily be measured and quantified using well known immunological techniques without undue experimentation.

Antigen binding molecules comprising modified forms of antibodies can be made from a whole precursor or parent antibody using techniques known in the art. Exemplary techniques are discussed in more detail below. In particularly preferred embodiments both the variable and constant regions of polypeptides comprising at least one antigen binding site of the invention are human. In one embodiment, fully human antibodies can be made using techniques that are known in the art. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make antibodies are described in U.S. Pat. Nos. 6,150,584; 6,458,592; 6,420,140. Other techniques are known in the art.

In other selected embodiments the variable regions of antibodies (usually derived from a non-human source) may be engineered or specifically tailored to improve the binding properties or reduce the immunogenicity of the antigen binding molecule.

The polypeptide comprising a binding site may comprise a heavy chain portion and other amino acid sequences or moieties not derived from an immunoglobulin molecule (e.g., additional bridging compositions of the invention). Such modifications are described in more detail below.

In one embodiment, the binding molecules have at least one antigen binding site specific for an antigen targeted for reduction or elimination, e.g., a cell surface antigen. In another embodiment, the target binding molecules have at least one antigen binding site specific for an antigen that can be used to detect the presence of a antigen (e.g., to detect a contaminant or diagnose a condition or disorder). In yet another embodiment, a binding molecule of the invention comprises at least one antigen site that targets the molecule to a specific site in a subject (e.g., to a tumor cell).

In one embodiment, an antigen binding site consists of a VH domain, e.g., derived from camelids, which is stable in the absence of a VL chain (Hamers-Castennan et al. 1993. Nature 363:446; Desmyter et al. 1996. Nat. Struct. Biol. 3:803; Desmyter, A., 1996. Nat. Struct. Biol. 3:803; Decanniere, K., et al. 1999. Structure 7:361; Davies et al. 1996. Protein Eng. 9:531; Kortt et al. 1995. J. Protein Chem. 14:167).

In one embodiment, a heavy chain variable portion and a light chain variable portion of a binding molecule that make up an antigen binding site of a molecule of the invention are present in the same polypeptide, e.g., as in a single chain antibody or a minibody (see e.g., U.S. Pat. No. 5,837,821 or WO 94/09817A1). In another embodiment, the heavy chain portion and the light chain portion of a polypeptide are present in different polypeptide chains, e.g., as in antibody molecules.

The antigen binding polypeptides of the invention may be multimeric molecules. In one embodiment, the antigen binding polypeptides are dimers. In one embodiment, the dimers of the invention are homodimers, comprising two identical monomeric subunits. In another embodiment, the dimers of the invention are heterodimers, comprising two non-identical monomeric subunits. The dimers comprise at least two polypeptide chains. In one embodiment, the binding molecules comprise two polypeptide chains. In another embodiment, the binding molecules comprise three polypeptide chains. In another embodiment, the binding molecules comprise four polypeptide chains.

As used herein, the term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor). Examples of tumors include, but are not limited to, pancreatic, lung, colon, breast, uterine, prostate, and ovarian tumors.

In one embodiment, a binding molecule of the invention binds to a tumor cell. Exemplary antibodies which comprise antigen binding sites that bind to antigens expressed on tumor cells are known in the art and include: Y2B8, Lym 1, Lym 2, C12, LL2, Her2, B1, MB1, BH3, B4, B72.3, CC49, p5E8, and 5E10. In a preferred embodiment, the polypeptide of the invention comprising at least one antigen binding site is a C2B8 antibody which binds to CD20. In another preferred embodiment, a polypeptide of the invention comprising at least one antigen binding site is a CC49 antibody which recognizes TAG72. In another preferred embodiment, the antigen binding site is specific for CD33. In another embodiment, the antigen binding site binds to BR96, IgG, Cd56, CD44v6, Her2/neu, Lewis, CD30, or Cripto.

As used herein, the term "autoimmune disease or disorder" refers to disorders or conditions in a subject wherein the immune system attacks the body's own cells, causing tissue destruction. Autoimmune diseases include general autoimmune diseases, i.e., in which the autoimmune reaction takes place simultaneously in a number of tissues, or organ specific autoimmune diseases, i.e., in which the autoimmune reaction targets a single organ. Examples of autoimmune diseases that can be diagnosed, prevented or treated by the methods and compositions of the present invention include, but are not limited to, Crohn's disease; Inflammatory bowel disease (IBD); systemic lupus erythematosus; ulcerative colitis; rheumatoid arthritis; goodpasture's syndrome; Grave's disease; Hashimoto's thyroiditis; pemphigus vulgaris; myasthenia gravis; scleroderma; autoimmune hemolytic anemia; autoimmune thrombocytopenic purpura; polymyositis and dermatomyositis; pernicious anemia; Sjögren's syndrome; ankylosing spondylitis; vasculitis; type I diabetes mellitus; neurological disorders, multiple sclerosis, and secondary diseases caused as a result of autoimmune diseases.

As used herein the term "inflammatory disease or disorder" includes diseases or disorders which are caused, at least in part, or exacerbated by inflammation, e.g., increased blood flow, edema, activation of immune cells (e.g., proliferation, cytokine production, or enhanced phagocytosis). Exemplary disorders include those in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, mitochondria, apoptosis, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents.

Acute inflammation is short-lasting, lasting only a few days. If it is longer lasting however, then it may be referred to as chronic inflammation.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they may last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or even longer, and are associated histologically with the presence of lymphocytes and macrophages and with proliferation of blood vessels and connective tissue. Recurrent inflammatory disorders include disorders which recur after a period of time or which have periodic episodes. Examples of recurrent inflammatory disorders include asthma and multiple sclerosis. Some disorders may fall within one or more categories.

Inflammatory disorders are generally characterized by heat, redness, swelling, pain and loss of function. Examples of causes of inflammatory disorders include, but are not limited to, microbial infections (e.g., bacterial, viral and fungal infections), physical agents (e.g., burns, radiation, and trauma), chemical agents (e.g., toxins and caustic substances), tissue necrosis and various types of immunologic reactions. Examples of inflammatory disorders include, but are not limited to, osteoarthritis, rheumatoid arthritis, acute and chronic infections (bacterial, viral and fungal); acute and chronic bronchitis, sinusitis, and other respiratory infections, including the common cold; acute and chronic gastroenteritis and colitis; acute and chronic cystitis and urethritis; acute respiratory distress syndrome; cystic fibrosis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; and burns (thermal, chemical, and electrical).

As used herein the term "affinity matrix" includes a matrix, such as agarose, controlled pore glass, or poly (styrenedivinyl)benzene to which an affinity ligand is attached. The affinity ligand binds to the affinity moiety and the contaminating polypeptides are not bound to the affinity ligand. The molecule of the invention with the affinity moiety can be eluted from the affinity matrix using known protocols.

As used herein, the phrase "subject that would benefit from administration of a binding molecule" includes subjects, such as mammalian subjects, that would benefit from administration of a binding molecule used, e.g., for detection of an antigen recognized by a binding molecule (e.g., for a diagnostic procedure) and/or from treatment with a binding molecule to reduce or eliminate the antigen recognized by the binding molecule. For example, in one embodiment, the subject may benefit from reduction or elimination of a soluble or particulate antigen from the circulation or serum (e.g., a toxin or pathogen) or from reduction or elimination of a population of cells expressing the target antigen (e.g., tumor cells). As described in more detail herein, the target binding molecule can be used in unconjugated form or can be conjugated, e.g., to a drug, prodrug, or an isotope.

As used herein, "alkyl" groups include saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups). The term "aliphatic group" includes organic moieties characterized by straight or branched-chains, typically having between 1 and 22 carbon atoms. In complex structures, the chains may be branched, bridged, or cross-linked. Aliphatic groups include alkyl groups, alkenyl groups, and alkynyl groups.

In certain embodiments, a straight-chain or branched-chain alkyl group may have 30 or fewer carbon atoms in its backbone, e.g., $C_1$-$C_{30}$ for straight-chain or $C_3$-$C_{30}$ for branched-chain. In certain embodiments, a straight-chain or branched-chain alkyl group may have 20 or fewer carbon atoms in its backbone, e.g., $C_1$-$C_{20}$ for straight-chain or $C_3$-$C_{20}$ for branched-chain, and more preferably 18 or fewer. Likewise, preferred cycloalkyl groups have from 4-10 carbon atoms in their ring structure, and more preferably have 4-7 carbon atoms in the ring structure. The term "lower alkyl" refers to alkyl groups having from 1 to 6 carbons in the chain, and to cycloalkyl groups having from 3 to 6 carbons in the ring structure.

Unless the number of carbons is otherwise specified, "lower" as in "lower aliphatic," "lower alkyl," "lower alkenyl," etc. as used herein means that the moiety has at least one and less than about 8 carbon atoms. In certain embodiments, a straight-chain or branched-chain lower alkyl group has 6 or fewer carbon atoms in its backbone (e.g., $C_1$-$C_6$ for straight-chain, $C_3$-$C_6$ for branched-chain), and more preferably 4 or fewer. Likewise, preferred cycloalkyl groups have from 3-8 carbon atoms in their ring structure, and more preferably have 5 or 6 carbons in the ring structure. The term "$C_1$-$C_6$" as in "$C_1$-$C_6$ alkyl" means alkyl groups containing 1 to 6 carbon atoms.

Moreover, unless otherwise specified the term alkyl includes both "unsubstituted alkyls" and "substituted alkyls," the latter of which refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, or aromatic (including heteroaromatic) groups.

An "arylalkyl" group is an alkyl group substituted with an aryl group (e.g., phenylmethyl (i.e., benzyl)). An "alkylaryl" moiety is an aryl group substituted with an alkyl group (e.g., p-methylphenyl (i.e., p-tolyl)). The term "n-alkyl" means a straight-chain (i.e., unbranched) unsubstituted alkyl group. An "alkylene" group is a divalent analog of the corresponding alkyl group. The terms "alkenyl" and "alkynyl" refer to unsaturated aliphatic groups analogous to alkyls, but which contain at least one double or triple carbon-carbon bond respectively. Suitable alkenyl and alkynyl groups include groups having 2 to about 12 carbon atoms, preferably from 2 to about 6 carbon atoms.

The term "aromatic group" or "aryl group" includes unsaturated and aromatic cyclic hydrocarbons as well as unsaturated and aromatic heterocycles containing one or more rings. Aryl groups may also be fused or bridged with alicyclic or heterocyclic rings that are not aromatic so as to form a polycycle (e.g., tetralin). An "arylene" group is a divalent analog of an aryl group. Aryl groups can also be fused or bridged with alicyclic or heterocyclic rings which are not aromatic so as to form a polycycle (e.g., tetralin).

The term "heterocyclic group" includes closed ring structures analogous to carbocyclic groups in which one or more of the carbon atoms in the ring is an element other than carbon, for example, nitrogen, sulfur, or oxygen. Heterocyclic groups may be saturated or unsaturated. Additionally, heterocyclic groups (such as pyrrolyl, pyridyl, isoquinolyl, quinolyl, purinyl, and furyl) may have aromatic character, in which case they may be referred to as "heteroaryl" or "heteroaromatic" groups.

Unless otherwise stipulated, aryl and heterocyclic (including heteroaryl) groups may also be substituted at one or more constituent atoms. Examples of heteroaromatic and heteroalicyclic groups may have 1 to 3 separate or fused rings with 3 to about 8 members per ring and one or more N, O, or S heteroatoms. In general, the term "heteroatom" includes atoms of any element other than carbon or hydrogen, preferred examples of which include nitrogen, oxygen, sulfuer, and phosphorus. Heterocyclic groups may be saturated or unsaturated or aromatic.

Examples of heterocycles include, but are not limited to, acridinyl; azocinyl; benzimidazolyl; benzofuranyl; benzothiofuranyl; benzothiophenyl; benzoxazolyl; benzthiazolyl; benztriazolyl; benztetrazolyl; benzisoxazolyl; benzisothiazolyl; benzimidazolinyl; carbazolyl; 4aH-carbazolyl; carbolinyl; chromanyl; chromenyl; cinnolinyl; decahydroquinolinyl; 2H,6H-1,5,2-dithiazinyl; dihydrofuro[2,3-b]tetrahydrofuran; furanyl; furazanyl; imidazolidinyl; imidazolinyl; imidazolyl; 1H-indazolyl; indolenyl; indolinyl; indolizinyl; indolyl; 3H-indolyl; isobenzofuranyl; isochromanyl; isoindazolyl; isoindolinyl; isoindolyl; isoquinolinyl; isothiazolyl; isoxazolyl; methylenedioxyphenyl; morpholinyl; naphthyridinyl; octahydroisoquinolinyl; oxadiazolyl; 1,2,3-oxadiazolyl; 1,2,4-oxadiazolyl; 1,2,5-oxadiazolyl; 1,3,4-oxadiazolyl; oxazolidinyl; oxazolyl; oxazolidinyl; pyrimidinyl; phenanthridinyl; phenanthrolinyl; phenazinyl; phenothiazinyl; phenoxathiinyl; phenoxazinyl; phthalazinyl; piperazinyl; piperidinyl; piperidonyl; 4-piperidonyl; piperonyl; pteridinyl; purinyl; pyranyl; pyrazinyl; pyrazolidinyl; pyrazolinyl; pyrazolyl; pyridazinyl; pyridooxazole; pyridoimidazole; pyridothiazole; pyridinyl; pyridyl; pyrimidinyl; pyrrolidinyl; pyrrolinyl; 2H-pyrrolyl; pyrrolyl; quinazolinyl; quinolinyl; 4H-quinolizinyl; quinoxalinyl; quinuclidinyl; tetrahydrofuranyl; tetrahydroisoquinolinyl; tetrahydroquinolinyl; tetrazolyl; 6H-1,2,5-thiadiazinyl; 1,2,3-thiadiazolyl; 1,2,4-thiadiazolyl; 1,2,5-thiadiazolyl; 1,3,4-thiadiazolyl; thianthrenyl; thiazolyl; thienyl; thienothiazolyl; thienooxazolyl; thienoimidazolyl; thiophenyl; triazinyl; 1,2,3-triazolyl; 1,2,4-triazolyl; 1,2,5-triazolyl; 1,3,4-triazolyl; and xanthenyl. Preferred heterocycles include, but are not limited to, pyridinyl; furanyl; thienyl; pyrrolyl; pyrazolyl; pyrrolidinyl; imidazolyl; indolyl; benzimidazolyl; 1H-indazolyl; oxazolidinyl; benzotriazolyl; benzisoxazolyl; oxindolyl; benzoxazolinyl; and isatinoyl groups. Also included are fused ring and spiro compounds containing, for example, the above heterocycles.

A common hydrocarbon aryl group is a phenyl group having one ring. Two-ring hydrocarbon aryl groups include naphthyl, indenyl, benzocyclooctenyl, benzocycloheptenyl, pentalenyl, and azulenyl groups, as well as the partially hydrogenated analogs thereof such as indanyl and tetrahydronaphthyl. Exemplary three-ring hydrocarbon aryl groups include acephthylenyl, fluorenyl, phenalenyl, phenanthrenyl, and anthracenyl groups.

Aryl groups also include heteromonocyclic aryl groups, i.e., single-ring heteroaryl groups, such as thienyl, furyl, pyranyl, pyrrolyl, imidazolyl, pyrazolyl, pyridinyl, pyrazinyl, pyrimidinyl, and pyridazinyl groups; and oxidized analogs thereof such as pyridonyl, oxazolonyl, pyrazolonyl, isoxazolonyl, and thiazolonyl groups. The corresponding hydrogenated (i.e., non-aromatic) heteromonocylic groups include pyrrolidinyl, pyrrolinyl, imidazolidinyl, imidazolinyl, pyrazolidinyl, pyrazolinyl, piperidyl and piperidino, piperazinyl, and morpholino and morpholinyl groups.

Aryl groups also include fused two-ring heteroaryls such as indolyl, isoindolyl, indolizinyl, indazolyl, quinolinyl, isoquinolinyl, phthalazinyl, quinoxalinyl, quinazolinyl, cinnolinyl, chromenyl, isochromenyl, benzothienyl, benzimidazolyl, benzothiazolyl, purinyl, quinolizinyl, isoquinolonyl, quinolonyl, naphthyridinyl, and pteridinyl groups, as well as the partially hydrogenated analogs such as chromanyl, isochromanyl, indolinyl, isoindolinyl, and tetrahydroindolyl groups. Aryl groups also include fused three-ring groups such as phenoxathiinyl, carbazolyl, phenanthridinyl, acridinyl, perimidinyl, phenanthrolinyl, phenazinyl, phenothiazinyl, phenoxazinyl, and dibenzofuranyl groups.

Some typical aryl groups include substituted or unsubstituted 5- and 6 membered single-ring groups. In another aspect, each Ar group may be selected from the group consisting of substituted or unsubstituted phenyl, pyrrolyl, furyl, thienyl, thiazolyl, isothiaozolyl, imidazolyl, triazolyl, tetrazolyl, pyrazolyl, oxazolyl, isooxazplyl, pyridinyl, pyrazinyl, pyridazinyl, and pyrimidinyl groups. Further examples include substituted or unsubstituted phenyl, 1-naphthyl, 2-naphthyl, biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl groups.

The term "amine" or "amino," as used herein, refers to an unsubstituted or substituted moiety of the formula —$NR^{a}R^{b}$, in which $R^{a}$ and $R^{b}$ are each independently hydrogen, alkyl, aryl, or heterocyclyl, or $R^{a}$ and $R^{b}$, taken together with the nitrogen atom to which they are attached, form a cyclic moiety having from 3 to 8 atoms in the ring. Thus, the term amino includes cyclic amino moieties such as piperidinyl or pyrrolidinyl groups, unless otherwise stated. Thus, the term "alkylamino" as used herein means an alkyl group having an amino group attached thereto. Suitable alkylamino groups include groups having 1 to about 12 carbon atoms, preferably from 1 to about 6 carbon atoms. The term amino includes compounds or moieties in which a nitrogen atom is covalently bonded to at least one carbon or heteroatom. The term "dialkylamino" includes groups wherein the nitrogen atom is bound to at least two alkyl groups. The term "arylamino" and "diarylamino" include groups wherein the nitrogen is bound to at least one or two aryl groups, respectively. The term "alkylarylamino" refers to an amino group which is bound to at least one alkyl group and at least one aryl group. The term "alkaminoalkyl" refers to an alkyl, alkenyl, or alkynyl group substituted with an alkylamino group. The term "amide" or "aminocarbonyl" includes compounds or moieties which contain a nitrogen atom which is bound to the carbon of a carbonyl or a thiocarbonyl group.

The term "alkylthio" refers to an alkyl group, having a sulfhydryl group attached thereto. Suitable alkylthio groups include groups having 1 to about 12 carbon atoms, preferably from 1 to about 6 carbon atoms.

The term "alkylcarboxyl" as used herein means an alkyl group having a carboxyl group attached thereto.

The term "alkoxy" as used herein means an alkyl group having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. Examples of alkoxy groups include methoxy, ethoxy, isopropyloxy, propoxy, butoxy, and pentoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc., as well as perhalogenated alkyloxy groups.

The term "acylamino" includes moieties wherein an amino moiety is bonded to an acyl group. For example, the acylamino group includes alkylcarbonylamino, arylcarbonylamino, carbamoyl and ureido groups.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "ether" or "ethereal" includes compounds or moieties which contain an oxygen bonded to two carbon atoms. For example, an ether or ethereal group includes "alkoxyalkyl" which refers to an alkyl, alkenyl, or alkynyl group substituted with an alkoxy group.

The term "nitro" means $-NO_2$; the term "halogen" or "halogeno" or "halo" designates $-F$, $-Cl$, $-Br$ or $-I$; the term "thiol," "thio," or "mercapto" means SH; and the term "hydroxyl" or "hydroxy" means $-OH$.

The term "acyl" refers to a carbonyl group that is attached through its carbon atom to a hydrogen (i.e., a formyl), an aliphatic group (e.g., acetyl), an aromatic group (e.g., benzoyl), and the like. The term "substituted acyl" includes acyl groups where one or more of the hydrogen atoms on one or more carbon atoms are replaced by, for example, an alkyl group, alkynyl group, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl; aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless otherwise specified, the chemical moieties of the compounds of the invention, including those groups discussed above, may be "substituted or unsubstituted." In some embodiments, the term "substituted" means that the moiety has substituents placed on the moiety other than hydrogen (i.e., in most cases, replacing a hydrogen), which allow the molecule to perform its intended function. Examples of substituents include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, and heteroaryl groups, as well as $(CR'R'')_{0-3}NR'R''$ (e.g., $-NH_2$), $(CR'R'')_{0-3}CN$ (e.g., $-CN$), $-NO_2$, halogen (e.g., $-F$, $-Cl$, $-Br$, or $-I$), $(CR'R'')_{0-3}C(halogen)_3$ (e.g., $-CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., $-SO_3H$), $(CR'R'')_{0-3}O(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}OH$ (e.g. $-OH$), $(CR'R'')_{0-3}COR'$, $(CR'R'')_{0-3}$ (substituted or unsubstituted phenyl), $(CR'R'')_{0-3}$ ($C_3$-$C_8$ cycloalkyl), $(CR'R'')_{0-3}CO_2R'$ (e.g., $-CO_2H$), and $(CR'R'')_{0-3}OR'$ groups, wherein R' and R" are each independently hydrogen, a $C_1$-$C_5$ alkyl, $C_2$-$C_5$ alkenyl, $C_2$-$C_5$ alkynyl, or aryl group; or the side chain of any naturally occurring amino acid.

In another embodiment, a substituent may be selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-10}NR'R''$ (e.g., $-NH_2$), $(CR'R'')_{0-10}CN$ (e.g., $-CN$), $NO_2$, halogen (e.g., F, Cl, Br, or I), $(CR'R'')_{0-10}C(halogen)_3$ (e.g., $-CF_3$), $(CR'R'')_{0-10}CH(halogen)_2$, $(CR'R'')_{0-10}CH_2(halogen)$, $(CR'R'')_{0-10}CONR'R''$, $(CR'R'')_{0-10}(CNH)NR'R''$, $(CR'R'')_{0-10}S(O)_{1-2}NR'R''$, $(CR'R'')_{0-10}CHO$, $(CR'R'')_{0-10}O(CR'R'')_{0-10}H$, $(CR'R'')_{0-10}S(O)_{0-3}R'$ (e.g., $-SO_3H$), $(CR'R'')_{0-10}O(CR'R'')_{0-10}H$(e.g., $-CH_2OCH_3$ and $-OCH_3$), $(CR'R'')_{0-10}S(CR'R'')_{0-3}H$ (e.g., $-SH$ and $-SCH_3$), $(CR'R'')_{0-10}OH$ (e.g., $-OH$), $(CR'R'')_{0-10}COR'$, $(CR'R'')_{0-10}$(substituted or unsubstituted phenyl), $(CR'R'')_{0-10}$($C_3$-$C_8$ cycloalkyl), $(CR'R'')_{0-10}CO_2R'$ (e.g., $-CO_2H$), or $(CR'R'')_{0-10}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a $-(CH_2)_2O(CH_2)_2-$ group.

It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more.

In some embodiments, a "substituent" may be, selected from the group consisting of, for example, halogeno, trifluoromethyl, nitro, cyano, $C_1$-$C_6$ alkyl, $C_2$-$C_6$ alkenyl, $C_2$-$C_6$ alkynyl, $C_1$-$C_6$ alkylcarbonyloxy, arylcarbonyloxy, $C_1$-$C_6$ alkoxycarbonyloxy, aryloxycarbonyloxy, $C_1$-$C_6$ alkylcarbonyl, $C_1$-$C_6$ alkoxycarbonyl, $C_1$-$C_6$ alkoxy, $C_1$-$C_6$ alkylthio, arylthio, heterocyclyl, aralkyl, and aryl (including heteroaryl) groups.

The invention pertains, at least in part, to a binding molecule of the formula (I):

$$Ab\text{-}(M\text{-}Z_r)_p \qquad (I)$$

wherein:

Ab is a polypeptide comprising at least one antigen binding site;

M is an independently selected branching moiety for each occurence;

Z is an independently selected drug moiety, affinity moiety, tag moiety, pharmokinetic moiety, or Ab for each occurrence;

r is an integer greater than or equal to 2; and p is an integer greater than or equal to 1, and pharmaceutically acceptable salts, esters, and prodrugs thereof, wherein Ab is linked to each M at a predetermined site on Ab.

The term "predetermined site" includes sites on the Ab which can be specifically attached to a M-Z, moiety. Predetermined sites include sites created using site directed mutagenesis. The predetermined site may be selected such that it is solvent accessible and does not substantially interfer with a binding site of the Ab, such as the Fc binding site. Examples of predetermined sites include exterior engineered cysteines. Preferably, exterior engineered cysteines are not involved in a structural disulfide bonds which may occur in the native-binding protein. Other predetermined sites may include side chains of unnatural amino acids, carboxylate groups and amino groups. The predetermined sites are selected such that a skilled artisan is able to control the number and location of the attached M-$Z_r$ moieties. In a further embodiment, the predetermined site is not a C-terminal carboxylate group or N-terminal amino group.

In a further embodiment, an Ab may comprise about 1 to about 20 predetermined sites, e.g., Ab may comprise 1, 2, 3, 4, 5, 6, 7, 8, 9, 10, 11, 12, 13, 14, 15, 16, 17, 18, 19 or 20 predetermined sites. In another further embodiment, p is from 1 to about 20, or from about 1 to about 10. In yet a further embodiment, p is 2 or 4.

In another further embodiment, r is an integer from about 2 to about 500, from 2 to about 300, from about 2 to about 100, or from about 2 to about 50.

The branching moiety, M, is selected such that it is capable of linking two or more Z moieties to a predetermined site on Ab. In a further embodiment, M is selected such that it is not comprised exclusively of natural or unnatural amino acid residues.

In an embodiment, the branching moiety comprises at least one thiol modification group capable of forming a thioether linkage (S) with a predetermined binding site on Ab, such as an engineered free cysteine in the Ab, and a second linkage with two or more Z moieties. Where the Z is a peptide, the branching moiety may form a second thioether bond with a native or engineered free cysteine in the Z protein or peptide In a further embodiment, the branching moiety (M) may comprise a spacer moiety. The branching moieties of the invention may be cleavable or non-cleavable. In one embodiment, the cleavable linking moiety is a redox-cleavable branching moiety, such that the branching moiety is cleavable in environments with a lower redox potential, such the cytoplasm and other regions with higher concentrations of molecules with free sulfhydryl groups. Examples of branching moieties that may be cleaved due to a change in redox potential include those containing disulfides. The cleaving stimulus can be provided upon intracellular uptake of the binding protein of the invention where the lower redox potential of the cytoplasm facilitates cleavage of the branching moiety. In another embodiment, a decrease in pH triggers the release of the Z moiety cargo into the target cell. The decrease in pH is implicated in many physiological and pathological processes, such as endosome trafficking, tumor growth, inflammation, and myocardial ischemia. The pH drops from a physiological 7.4 to 5-6 in endosomes or 4-5 in lysosomes. Examples of acid sensitive branching moieties which may be used to target lysosomes or endosomes of cancer cells, include those with acid-cleavable bonds such as those found in acetals, ketals, orthoesters, hydrazones, trityls, cis-aconityls, or thiocarbamoyls (see for example, Willner et al., (1993), *Bioconj. Chem.*, 4: 521-7; U.S. Pat. Nos. 4,569,789, 4,631,190, 5,306,809, and 5,665,358). Other exemplary acid-1-sensitive branching moieties comprise dipeptide sequences Phe-Lys and Val-Lys (King et al., (2002), *J. Med. Chem.*, 45: 4336-43). The cleaving stimulus can be provided upon intracellular uptake trafficking to low pH endosomal compartments (e.g. lysosomes). Other exemplary acid-cleavable branching moieties are the moieties that contain two or more acid cleavable bonds for attachment of two or more drug moieties (King et al., (1999), *Bioconj. Chem.*, 10: 279-88; WO 98/19705).

Cleavable branching moieties may be sensitive to biologically supplied cleaving agents that are associated with a particular target cell, for example, lysosomal or tumor-associated enzymes. Examples of branching moieties that can be cleaved enzymatically include, but are not limited to, peptides and esters. Exemplary enzyme cleavable branching moieties include those that are sensitive to tumor-associated proteases such as Cathepsin B or plasmin (Dubowchik et al., (1999), *Pharm. Ther.*, 83: 67-123; Dubowchik et al., (1998), *Bioorg. Med. Chem. Lett.*, 8: 3341-52; de Groot et al., (2000), *J. Med. Chem.*, 43: 3093-102; de Groot et al., (1999)m 42: 5277-83). Cathepsin B-cleavable sites include the dipeptide sequences valine-citrulline and phenylalanine-lysine (Doronina et al., (2003), *Nat. Biotech.*, 21(7): 778-84); Dubowchik et al., (2002), *Bioconjug. Chem.*, 13: 855-69). Other exemplary enzyme-rcleavable sites include those formed by oligopeptide sequences of 4 to 16 amino acids (e.g., Suc-O-Ala-Leu-Ala-Leu) which recognized by trouse proteases such as Thimet Oliogopeptidase (TOP), an enzyme that is preferentially released by neutrophils, macrophages, and other granulocytes (U.S. patent application Ser. No. 09/789,442, filed Jun. 11, 2001).

Alternatively, the cleavable branching moieties may not be cleavable at the site of the target cells, but cleavable at the site of a non-target cell. In other words, the branching moiety may be more stable upon localization to the target cell. Stable branching moeties are preferably introduced into target binding proteins to form binding proteins of the invention that may be used for diagnostic purposes. Selectively stable branching moieties therefore, provide a means to reduce non-specific localization of diagnostic antibodies at non-target sites. Preferred stable branching moieties include "metabolizable" sites comprising thiourea groups, peptides, esters, or disulfides that are selectively metabolized by non-target cells (Haseman et al., (1986), *J. Nucl. Med.,* 12: 455-60). Nonspecific localization of diagnostic modified binding protein may be reduced by administering an exogenous enzyme or chemical cleaving agent which selectively cleaves a cleavable branching moiety at one or more non-target cells within the host. For example, the cleaving agent may be a compound that alters the pH or redox state at the non-target site (e.g. reducing kidney toxicity by acidifying the urine) or a compound that increases the reducing state of the non-target site. Exemplary urine acidifying agents include ammonium chloride (U.S. Pat. No. 5,171,563). In another embodiment, the linking moiety may be susceptible to cleavage by serum enzymes (e.g. serum esterases). Examples, of branching moieties susceptible to plasma hydrolysis include certain derivatives of glycolamides (Nielsen et al., (1987), *J. Med. Chem.,* 30(3): 451-4; U.S. Pat. No. 5,171,563).

In another embodiment, the cleavable branching moiety may comprise a tripartite releasable Polyethylene Glycol (rPEG) cleavage site for controlled hydrolytic release of a Z moiety, such as a cytotoxin (Greenwald et al., (2003), *Bioconjug. Chem.,* 14: 395-403). rPEG cleavage sites may contain a variable number of PEG substituents attached by cleavable groups (e.g., those containing ester, carbamate, or carbonate bonds) and non-cleavable groups (e.g. a p-substituted benzyl alcohols) to free amino groups of a peptide sequence. The hydrolysis rate of the rPEG cleavage site can be modified by the number of PEG groups and the choice of substituents on the cleavable and non-cleavable groups. Such branching moieties can be attached to one or more Z moieties with appropriate chemically reactive functional groups (e.g. a free amine or hydroxyl). In one embodiment, the branching moiety can be directly attached to one or more appropriately functionalized Z moieties via a covalent bond, such that the Z moiety may be released unaltered or attached to vestiges of the cleavable group. In another embodiment, the Z moiety may first be derivatized in preparation for direct reaction with the reactive functional group on the cleavable branching moiety.

In an embodiment, Z is an affinity moiety. Affinity moieties include moieties which would allow the separation of an affinity moiety labeled binding molecule of the invention from a mixture by contacting the affinity moiety with an affinity matrix. Examples of affinity moieties include, but are not limited to, biotin.

In another embodiment, Z is a drug moiety. The term "drug moiety" includes agents which would be beneficial to the subject when delivered by an binding molecule of the invention. The drug moieties may include, but are not limited to anti-inflammatory, anticancer, antiinfective (e.g., anti-fungal, antibacterial, anti-parasitic, anti-viral, etc.), or anesthetic agents. In a further embodiment, the drug moiety is an anticancer or cytotoxic agent. In a further embodiment, a binding molecule of the invention comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 60-100, 100-500 or more Z groups which are drug moieties. In another embodiment, each Z moiety is a maytansinoid.

Preferred drug moieties for use in the present invention are cytotoxic drugs, particularly those which are used for cancer therapy, e.g., anticancer agents. As used herein, "a cytotoxin or cytotoxic agent" or "anticancer agent" means any agent that is detrimental to the growth and proliferation of cells and may act to reduce, inhibit or destroy a cell or malignancy. Exemplary cytotoxins include, but are not limited to, radionuclides, biotoxins, enzymatically active toxins, cytostatic or cytotoxic therapeutic agents, prodrugs, immunologically active ligands and biological response modifiers such as cytokines. Any cytotoxin that acts to retard or slow the growth of immunoreactive cells or malignant cells is within the scope of the present invention.

Exemplary cytotoxins include, in general, cytostatic agents, alkylating agents, antimetabolites, anti-proliferative agents, tubulin binding agents, hormones and hormone antagonists, and the like. Exemplary cytostatics that are compatible with the present invention include alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine. Other preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, caminomycin, daunorubicin (daunomycin), doxorubicin, aminopterin, methotrexate, methopterin, mithramycin, streptonigrin, dichloromethotrexate, mitomycin C, actinomycin-D, porfiromycin, 5-fluorouracil, floxuridine, florafur, 6-mercaptopurine, cytarabine, cytosine arabinoside, podophyllotoxin, or podophyllotoxin derivatives such as etoposide or etoposide phosphate, melphalan, vinblastine, vincristine, leurosidine, vindesine, leurosine and the like. Still other cytotoxins that are compatible with the teachings herein include taxol, taxane, cytochalasin B, gramicidin D, ethidium bromide, emetine, tenoposide, colchicin, dihydroxy anthracin dione, mitoxantrone, procaine, tetracaine, lidocaine, propranolol, and puromycin and analogs or homologs thereof. Hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e.g. aminogluthetimide are also compatible with the teachings herein. As noted previously, one skilled in the art may make chemical modifications to the desired compound in order to make reactions of that compound more convenient for purposes of preparing conjugates of the invention.

Examples of drug moieties include doxorubicin, etoposide, taxane, paclitaxel, fluorouracyl, mitomycin, camptothecin, gemcitabine, geldanamycin, epothilone, cephalostatin, tubulin inhibitors, a vinca alkaloid, proteasome inhibitors, neocarzinostatin, calicheamicin, maytansinoids, (RS)-cyclophosphamide, 6-mercaptopurines, auristatin E, daunorubicin, and derivatives or analogs thereof. The drug moieties may be attached to the remainder of the binding molecule through any atom which allows the resulting binding molecule and/or drug moiety to perform its intended function. The drug moieties also include pharmaceutically acceptable prodrugs, salts, esters, amides, and ethers of the drug moieties described herein.

In another is a nucleic acid, such as DNA or RNA. The nucleic acid may be an sense nucleic acid, RNAi, or another desirable nucleic acid construct.

Examples of certain drug moieties of the invention are shown below in Table 1:

TABLE 1

| Structure | Name | Possible Method of Action |
|---|---|---|
| 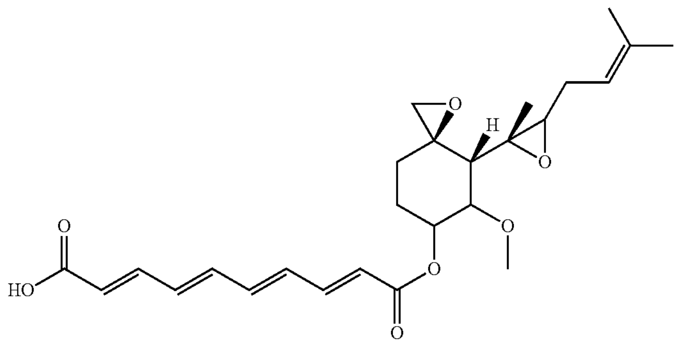 [SMILES: COC1C(OC(=O)/C=C/C=C/C=C/C=C/C(=O)O)CC[C@]2(CO2)[C@@H]1[C@@]1(C)OC1CC=C(C)C] | Fumagillin | Inhibitor of endothelial cell proliferation and angiogenesis. |
| 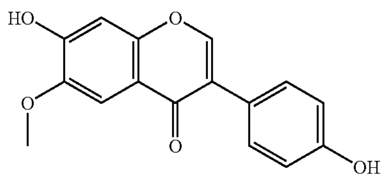 [SMILES: COc1cc2c(=O)c(-c3ccc(O)cc3)coc2cc1O] | Genistein | Antiangiogenic agent, down-regulates the transcription of genes involved in controlling angiogenesis. |
| 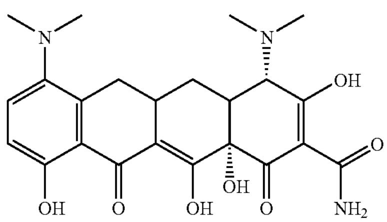 [SMILES: CN(C)c1ccc(O)c2c1CC1CC3[C@H](N(C)C)C(O)=C(C(N)=O)C(=O)[C@@]3(O)C(O)=C1C2=O] | Minocycline | Inhibits endothelial cell proliferation and angiogenesis. |
| 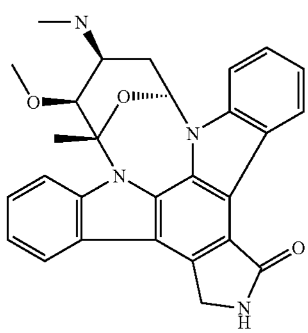 [SMILES: CN[C@H]1C[C@@H]2O[C@@](C)([C@H]1OC)n1c3ccccc3c3c4c(c5c6ccccc6n2c5c31)C(=O)NC4] | Staurosporine | Blocks angiogenesis by inhibiting the upregulation of VEGF expression in tumor cells. |
| 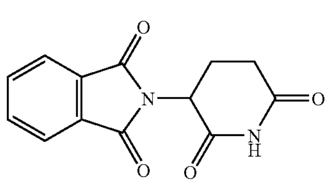 [SMILES: O=C1CCC(N2C(=O)c3ccccc3C2=O)C(=O)N1] | (±)-Thalidomide | Selectively inhibits biosynthesis of tumor necrosis factor α (TNF-α); inhibits angiogenesis. |
| 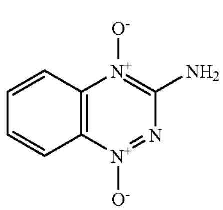 [SMILES: Nc1n[n+]([O-])c2ccccc2[n+]1[O-]] | 3-Amino-1,2,4-benzotriazine 1,4-dioxide | Hypoxia-activated antineoplastic agent. |

TABLE 1-continued

| Structure | Name | Possible Method of Action |
|---|---|---|
| 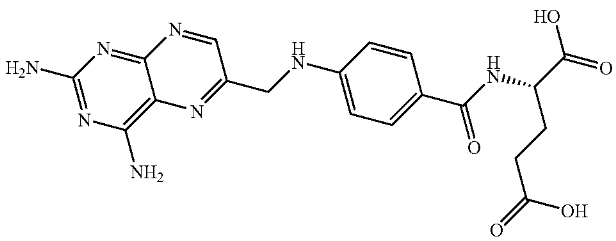 [SMILES: Nc1nc(N)c2nc(CNc3ccc(C(=O)N[C@@H](CCC(=O)O)C(=O)O)cc3)cnc2n1] | Aminopterin | Folic acid antagonist; blocks thymidine biosynthesis by inhibiting dihydrofolate reductase. More potent, but more toxic, than methotrexate. |
| 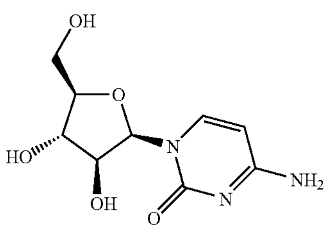 [SMILES: Nc1ccn([C@@H]2O[C@H](CO)[C@@H](O)[C@@H]2O)c(=O)n1] | Cytosine β-D-arabinofuranoside | Selective inhibitor of DNA synthesis. |
| 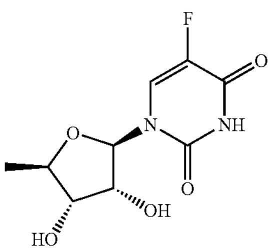 [SMILES: C[C@H]1O[C@@H](n2cc(F)c(=O)[nH]c2=O)[C@H](O)[C@@H]1O] | 5-Fluoro-5'-deoxyuridine | Inhibits proliferation of tumors, cell lines or fibroblasts transformed by H-Ras or Trk oncogenes. |
| 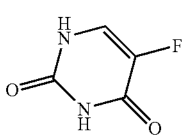 | 5-Fluorouracil | Inhibits thymidylate synthetase and depletes dTTP; it forms nucleotides that can be incorporated into RNA and DNA and induces p53-dependent apoptosis. |
| 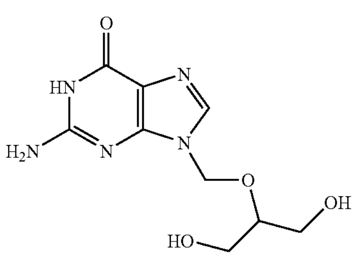 [SMILES: Nc1nc2c(ncn2COC(CO)CO)c(=O)[nH]1] | Ganciclovir | In suicide gene therapy of solid tumors, the gene for *Herpes simplex* virus thymidine kinase is delivered to tumor cells and expressed, which in turn activates ganciclovir cytotoxicity. |
| 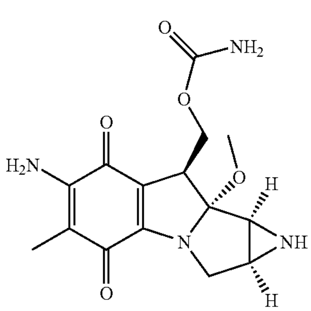 [SMILES: CO[C@@]12[C@H](COC(N)=O)C3=C(C(=O)C(C)=C(N)C3=O)N1C[C@@H]1N[C@@H]12] | Mitomycin C | Inhibits DNA synthesis, nuclear division, and proliferation of cancer cells. |

TABLE 1-continued

| Structure | Name | Possible Method of Action |
|---|---|---|
| 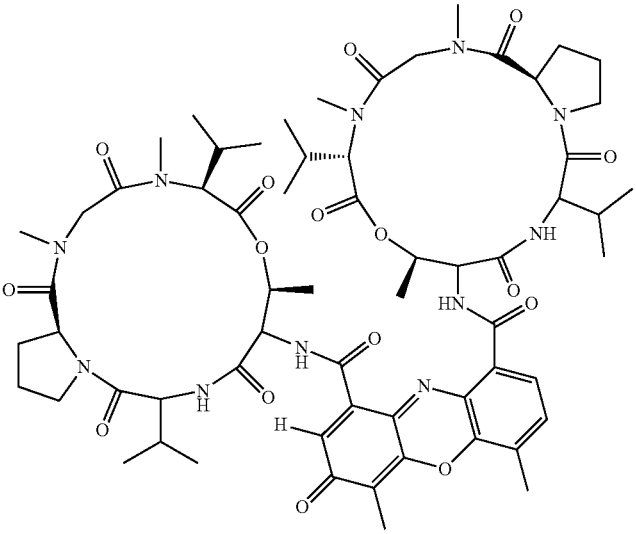 [SMILES: Cc1c2oc3c(C)ccc(C(=O)NC4C(=O)NC(C(C)C)C(=O)N5CCC[C@@H]5C(=O)N(C)CC(=O)N(C)[C@@H](C(C)C)C(=O)O[C@@H]4C)c3nc-2c(C(=O)NC2C(=O)NC(C(C)C)C(=O)N3CCC[C@H]3C(=O)N(C)CC(=O)N(C)[C@@H](C(C)C)C(=O)O[C@H]2C)cc1=O] | Actinomycin D | Inhibits cell proliferation by complexing to DNA and blocking the production of mRNA by RNA polymerase; induces apoptosis. |
| 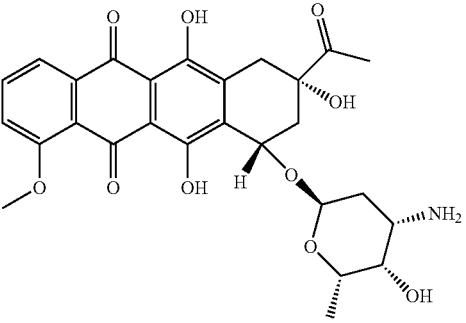 [SMILES: COc1cccc2c1C(=O)c1c(O)c3c(c(O)c1C2=O)C[C@@](O)(C(C)=O)C[C@@H]3O[C@H]1C[C@H](N)[C@H](O)[C@H](C)O1] | Daunorubicin | Complexes to DNA and blocks production of mRNA by RNA polymerase. |
| 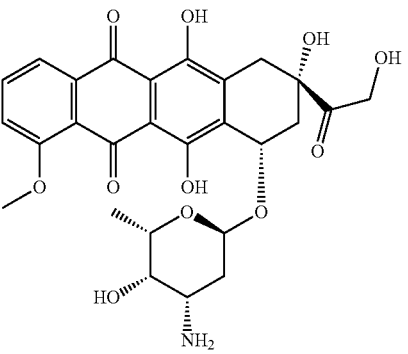 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1] | Doxorubicin | Binds to DNA and inhibits reverse transcriptase and RNA polymerase. |
| 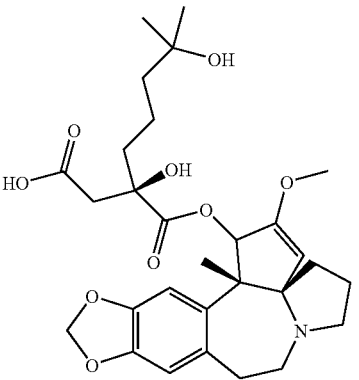 [SMILES: COC1=C[C@]23CCCN2CCc2cc4c(cc2[C@]3(C)C1OC(=O)[C@@](O)(CCCC(C)(C)O)CC(=O)O)OCO4] | Homoharringtonine | Binds to the 80S ribosome in eukaryotic cells and inhibits protein synthesis by interfering with chain elongation. |

TABLE 1-continued

| Structure | Name | Possible Method of Action |
|---|---|---|
| 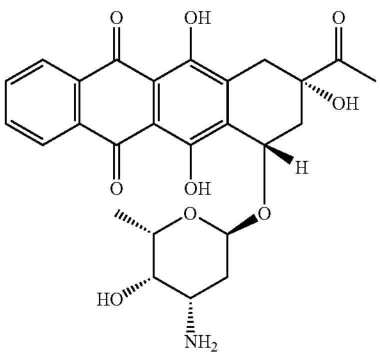 [SMILES: CC(=O)[C@]1(O)Cc2c(O)c3c(c(O)c2[C@@H](O[C@H]2C[C@H](N)[C@H](O)[C@H](C)O2)C1)C(=O)c1ccccc1C3=O] | Idarubicin | Anti-leukemia agent with higher DNA binding capacity and greater cytotoxicity than daunorubicin. |
| 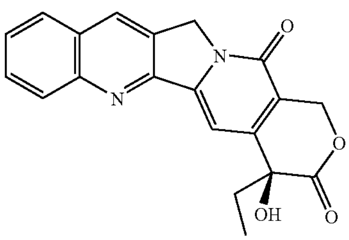 [SMILES: CC[C@@]1(O)C(=O)OCc2c1cc1n(c2=O)Cc2cc3ccccc3nc2-1] | S(+)-Camptothecin | Binds irreversibly to the DNA-topoisomerase I complex leading to the irreversible cleavage of DNA and the destruction of cellular topoisomerase I by the ubiquitin-proteasome pathway. Induces apoptosis in many normal and tumor cell lines. |
| 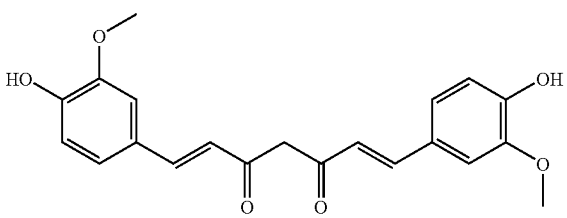 [SMILES: COc1cc(/C=C/C(=O)CC(=O)/C=C/c2ccc(O)c(OC)c2)ccc1O] | Curcumin | Potent inhibitor of protein kinase C, EGFR tyrosine kinase and IκB kinase. Induces apoptosis in cancer cells. |
| 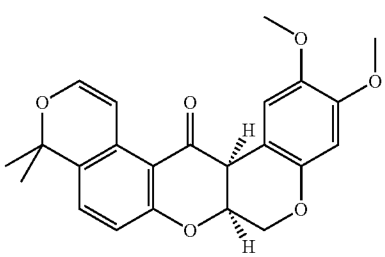 | (−)-Deguelin | Inhibitor of activated Akt. Does not affect MAPK, ERK1/2 or JNK. |
| 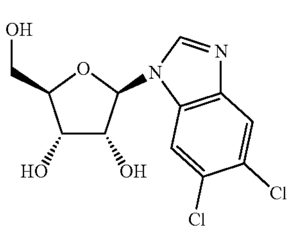 [SMILES: OC[C@H]1O[C@@H](n2cnc3cc(Cl)c(Cl)cc32)[C@H](O)[C@@H]1O] | 5,6-Dichlorobenz-imidazole 1-β-D-ribofuranoside | Inhibitor of RNA synthesis, causes premature termination of transcription. |

TABLE 1-continued

| Structure | Name | Possible Method of Action |
|---|---|---|
| 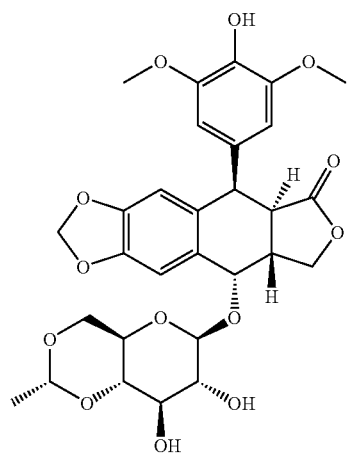 | Etoposide | Binds to the DNA-topoisomerase II complex to enhance cleavage and inhibit religation; inhibits synthesis of the oncoprotein Mdm2 and induces apoptosis in tumor lines that overexpress Mdm2. |
| 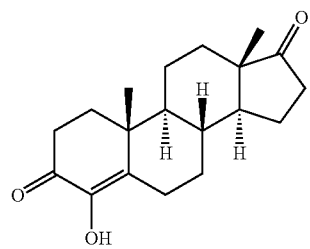 | Formestane | Aromatase inhibitor |
| 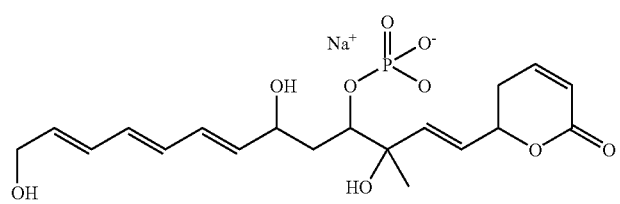 [SMILES: CC(O)(/C=C/C1CC=CC(=O)O1)C(CC(O)/C=C/C=C/C=C/CO)OP(=O)([O-])O ; [Na+]] | Fostriecin | Interferes with the reversible phosphorylation of proteins that are critical for progression through the cell cycle. |
| 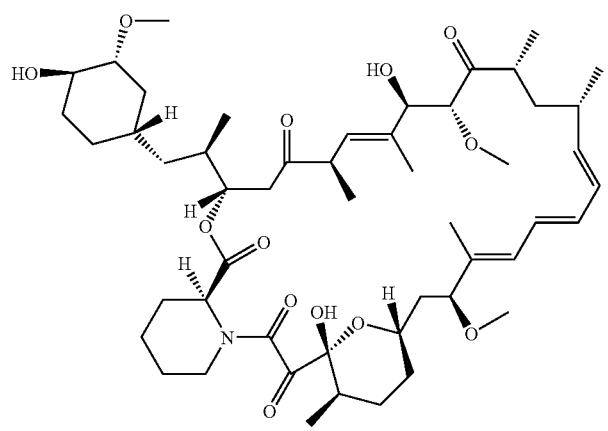 | Rapamycin | Inhibition of the molecular target of rapamycin (mTOR) mediates the antiproliferative and anticancer activity of rapamycin by blocking the PI3K/Akt pathway. |
| 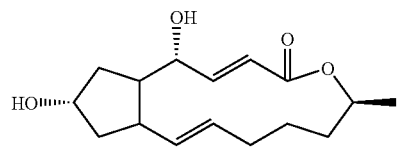 [SMILES: C[C@H]1CCC/C=C/C2C[C@H](O)CC2[C@H](O)/C=C/C(=O)O1] | Brefeldin A | Disrupts the structure and function of the Golgi apparatus. An activator of the sphingomyelin cycle. |

TABLE 1-continued

| Structure | Name | Possible Method of Action |
|---|---|---|
| 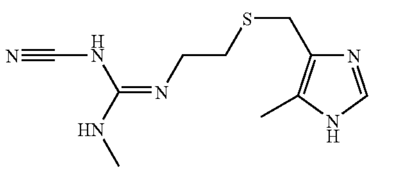 [SMILES: CN/C(=N/CCSCc1nc[nH]c1C)NC#N] | Cimetidine | $H_2$ histamine receptor antagonist; $I_1$ imidazoline receptor agonist; anti-ulcer agent. Blocks cancer metastasis by inhibiting the expression of E-selectin on the surface of endothelial cells, thus blocking tumor cell adhesion. |
| 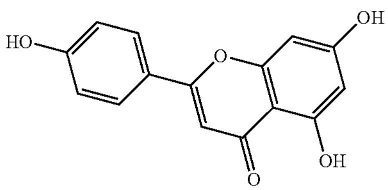 [SMILES: O=c1cc(-c2ccc(O)cc2)oc2cc(O)cc(O)c12] | Apigenin | Inhibits cell proliferation by arresting the cell cycle at the G2/M phase. Inhibition of growth through cell cycle arrest and induction of apoptosis appear to be related to induction of p53. Inhibitory effects on tumor promotion may also be due to inhibition of kinase activity and the resulting suppression of oncogene expression. It has also been reported to inhibit topoisomerase I catalyzed DNA religation and enhance gap junctional intercellular communication. |
| 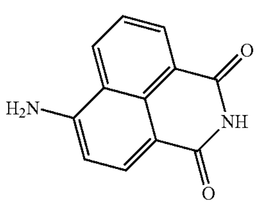 [SMILES: Nc1ccc2c3c(cccc13)C(=O)NC2=O] | 4-Amino-1,8-naphthalimide | Sensitizes cells to radiation-induced cell damage and enhances the cytotoxicity of 1-methyl-3-nitro-1-nitrosoguanidine. |
| 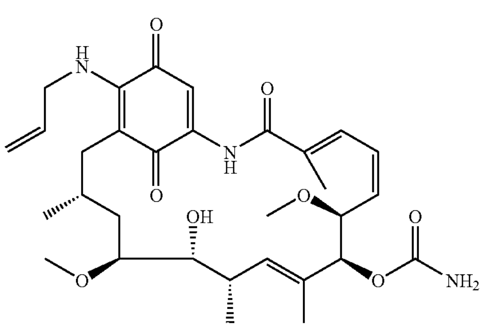 [SMILES: C=CCNC1=C2C[C@@H](C)C[C@H](OC)[C@H](O)[C@@H](C)/C=C(\C)[C@H](OC(N)=O)[C@@H](OC)/C=C\C=C(/C)C(=O)NC(=CC1=O)C2=O] | 17-(Allylamino)-17-demethoxygeldanamycin | Inhibits the activity of oncogenic proteins such as N-ras, Ki-ras, c-Akt, and p185$^{erB2}$. Induces apoptosis. |
| | Vincristine | Antimitotic agent. Inhibits microtubule assembly by binding tubulin and inducing self-association; depolymerizes pre-existing microtubules. Induces apoptosis in several tumor cell lines. | or derivatives, prodrugs, esters, amides, or pharmaceutically acceptable salts thereof. Derivatives include modifications to drugs identified herein which may improve or not significantly reduce a particular drug's desired therapeutic activity.

In another embodiment, the anticancer agent is an angiogenesis inhibitor. Examples of angiogenesis inhibitors include: Angiostatin K1-3, DL-α-Difluoromethyl-ornithine, Endostatin, Fumagillin, Genistein, Minocycline, Staurosporine, and (±)-Thalidomide.

In another embodiment, the anticancer agent is a DNA-intercalator or cross-linker. Examples of such anticancer agents include, but are not limited to, Bleomycin, Carboplatin, Carmustine, Chlorambucil, Cyclophosphamide, cis-Diammineplatinum(II) dichloride (Cisplatin), Melphalan, Mitoxantrone, and Oxaliplatin.

In another embodiment, the anticancer agent is a DNA synthesis inhibitor. Examples of DNA synthesis inhibitors include, but are not limited to, (±)-Amethopterin (Methotrexate), 3-Amino-1,2,4-benzotriazine 1,4-dioxide, Aminopterin, Cytosine β-D-arabinofuranoside, 5-Fluoro-5'-deoxyuridine, 5-Fluorouracil, Ganciclovir, Hydroxyurea, and Mitomycin C.

In another embodiment, the anticancer agent is a DNA-RNA transcription regulator. Examples of such transcription regulators include Actinomycin D, Daunorubicin, Doxorubicin, Homoharringtonine, and Idarubicin.

In another embodiment, the anticancer agent is an enzyme inhibitor. Examples of enzyme inhibitors include but are not limited to, S(+)-Camptothecin, Curcumin, (−)-Deguelin, 5,6-Dichlorobenz-imidazole 1-β-D-ribofuranoside, Etoposide, Formestane, Fostriecin, Hispidin, 2-Imino-1-imidazolidineacetic acid (Cyclocreatine), Mevinolin, Trichostatin A, Tyrphostin AG 34, and Tyrphostin AG 879.

In another embodiment, the anticancer agent include agents which regulate genes. Examples of gene regulators include 5-Aza-2'-deoxycytidine, 5-Azacytidine, Cholecalciferol (Vitamin $D_3$), 4-Hydroxytamoxifen, Melatonin, Mifepristone, Raloxifene, trans-Retinal (Vitamin A aldehydes), Retinoic acid, Vitamin A acid, 9-cis-Retinoic Acid, 13-cis-Retinoic acid, Retinol (Vitamin A), Tamoxifen, and Troglitazone.

In another embodiment, the anticancer agent is a microtubule inhibitor. Examples of microtubule inhibitors include Colchicine, Dolastatin 15, Nocodazole, Paclitaxel, Podophyllotoxin, Rhizoxin, Vinblastine, Vincristine, Vindesine, and Vinorelbine (Navelbine).

In another embodiment, the anticancer agent is 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-o, Rapamycin, Sex hormone-binding globulin, and Thapsigargin.

Other anticancer agents also include compounds of the formula:

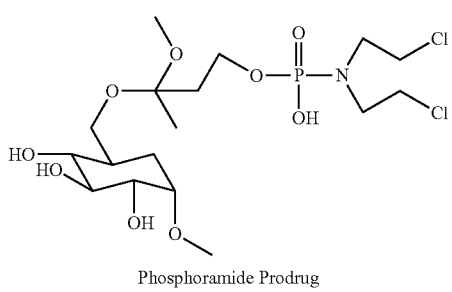

Phosphoramide Prodrug

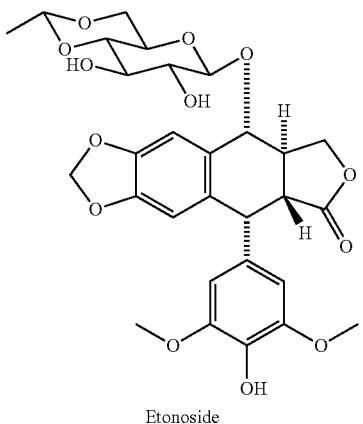

Etonoside

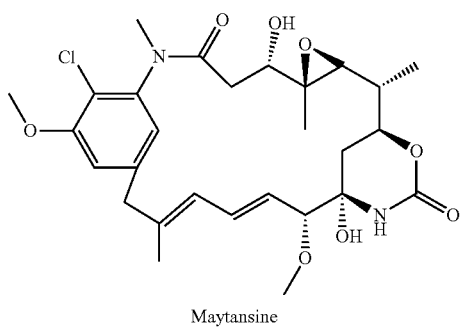

Maytansine

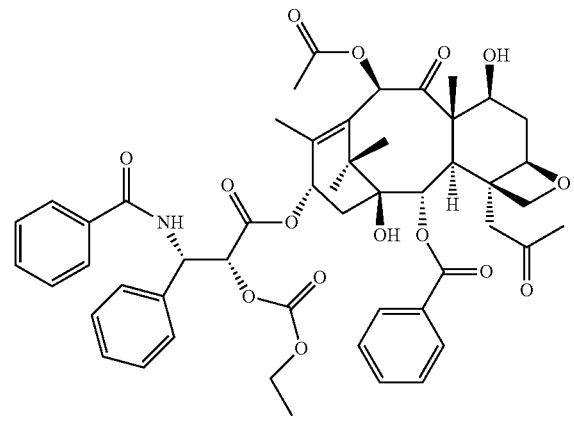

Paclitaxel

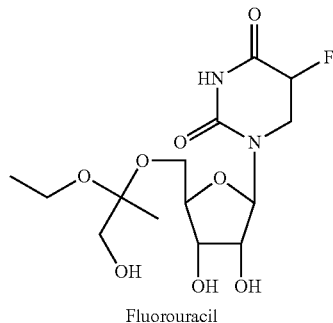
Fluorouracil
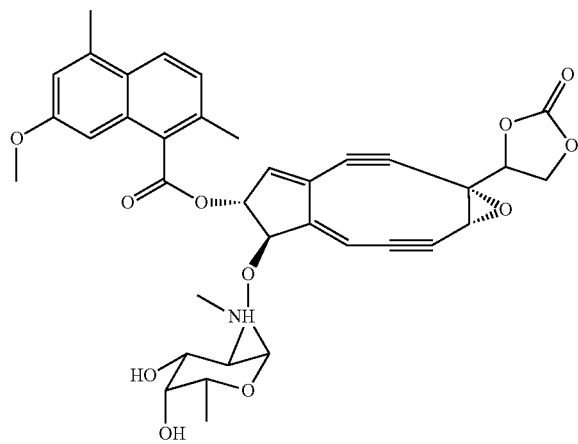
Neocarzinostatin
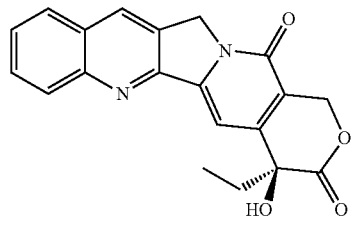
Camptothecin
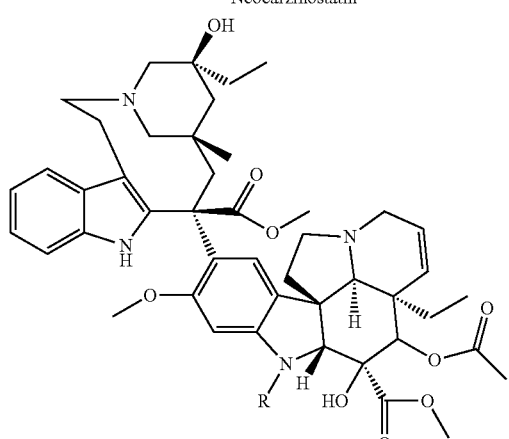
Vinca alkaloids
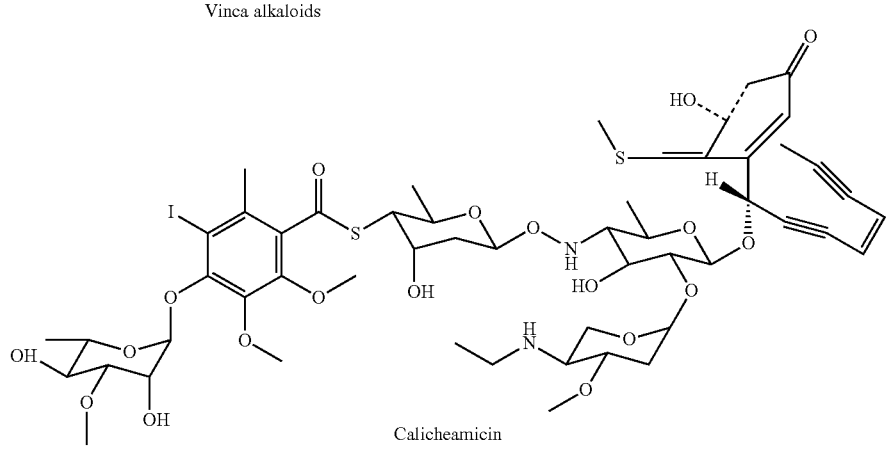
Calicheamicin and pharmaceutically acceptable esters, prodrugs, derivatives and salts, thereof.

In one embodiment, the drug moiety is a maytansinoid of the formula (IV):

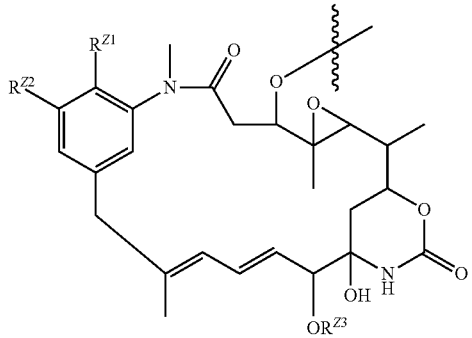

(IV)

wherein
$R^{Z1}$ is halogen or hydrogen; and
$R^{Z2}$ and $R^{Z3}$ are each hydrogen or lower alkyl.

In a further embodiment, $R^{Z1}$ is chlorine and $R^{Z2}$ and $R^{Z3}$ are each methyl.

In another embodiment, the drug moiety (Z) is a taxane derivative of formula (V):

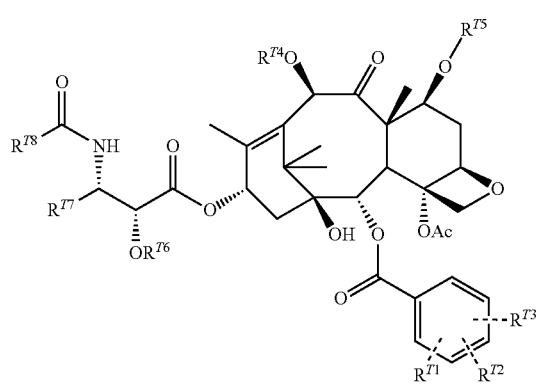

(V)

wherein:
$R^{T1}$, $R^{T2}$, and $R^{T3}$ are each independently hydrogen, an electron withdrawing group, or an electron donating group;
$R^{T4}$, $R^{T5}$, $R^{T6}$ are each independently a covalent bond to L, hydrogen, heterocyclic, an ester, an ether, a carbamate of the formula —$CONR^{T10}R^{T11}$, wherein $R^{T10}$ and $R^{T11}$ are each independently hydrogen, alkyl, alkenyl, alkynyl, acyl or aryl, provided that one of $R^{T4}$, $R^{T5}$, and $R^{T6}$ is a covalent bond to L;
$R^{T7}$ is alkyl, alkenyl, alkynyl, acyl or aryl; and
$R^{T8}$ is alkoxy or aryl.

In another embodiment, $R^{T1}$ is halogen (e.g., fluorine, chlorine, bromine, etc.), $NO_2$, CN, $CHF_2$, $CF_3$, —$OCH_3$, —$OCH_2CH_3$, or $NR^{T11}R^{T12}$, where $R^{T11}$ and $R^{T12}$ are each independently hydrogen, alkyl (e.g., $C_1$-$C_{10}$ alkyl), alkenyl, alkynyl, or aryl.

$R^{T4}$ is —$COC_2H_5$, —$CH_2CH_3$, —$CONHCH_2CH_3$, —CO— morpholino, —CO-piperidino, —CO-piperazino, or —CO—N-methylpiperizino.

In another embodiment, $R^{T1}$, $R^{T2}$, and $R^{T3}$ are H or methoxy. In a further embodiment, $R^{T1}$ is in the meta position when $R^{T2}$ and $R^{T3}$ are hydrogen or methoxy.

In another embodiment, the drug moiety (Z) is a doxorubicin derivative of the formula (VI):

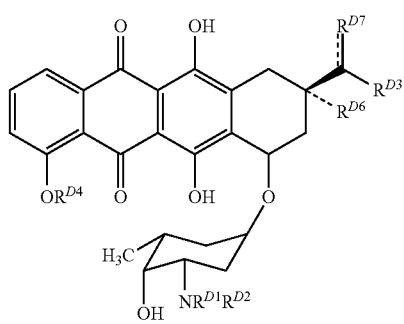

(VI)

wherein:
Y is O or $NR^{D5}$, wherein $R^{D5}$ is alkyl or hydrogen;
$R^{D1}$ and $R^{D2}$ are each hydrogen, or taken together a moiety of the formula (VIa):

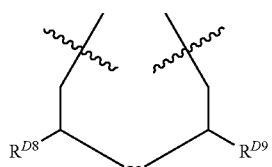

(VIa)

wherein
$R^{D3}$ is alkyl;
$R^{D4}$ is alkyl or hydrogen;
$R^{D6}$ is hydroxy or alkyl;
$R^{D7}$ is O or a covalent bond to L;
$R^{D8}$ and $R^{D9}$ are each a covalent bond to L, hydrogen, alkoxy, or alkyl; provided that one of $R^{D1}$, $R^{D2}$, and $R^{D7}$ is a covalent bond to L.

In a further embodiment, $R^{D5}$ is methyl. In another further embodiment, $R^{D9}$ is alkoxy.

As previously alluded to, compatible cytotoxins may comprise a prodrug. As used herein, the term "prodrug" refers to a precursor or derivative form of a drug moiety that is less cytotoxic to tumor cells compared to the parent drug and is capable of being enzymatically activated or converted into the more active parent form. Prodrugs compatible with the invention include, but are not limited to, phosphate-containing prodrugs, thiophosphate-containing prodrugs, sulfate containing prodrugs, peptide containing prodrugs, P-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. Further examples of cytotoxic drugs that can be derivatized into a prodrug form for use in the present invention comprise those chemotherapeutic agents described above.

In another embodiment, Z is a tag moiety. Examples of tag moieties include fluorescent and radiolabels. Binding molecules comprising at least one tag moiety may be used, for example, to image cells expressing the antigen of interest. Examples of tag moieties include, but are not limited to, radioisotopes (e.g., $^{123}$Iodine, $^{125}$Iodine, $^{131}$Iodine, $^{105}$Rhodium, $^{67}$Gallium, $^{153}$Sm, $^{177}$Lu, $^{186}$Re, $^{188}$Re, $^{166}$Ho, $^{67}$Cu, $^{90}$Y, $^{111}$Indium, $^{18}$-Fluorine, or $^{99m}$Technetium (Tc99m)), an optically active molecule, e.g., a fluorescent dye (e.g., Fluorescein), a luminescent molecule (e.g., luminal), or a bioluminescent molecule (e.g., luciferase, luciferin, and aequorin). The radionuclides act by producing ionizing radiation which causes multiple strand breaks in nuclear DNA, leading to cell death. The isotopes used to produce therapeutic conjugates typically produce high energy α- or β-particles which have a short path length. Such radionuclides kill cells to which they are in close proximity, for example neoplastic cells to which the conjugate has attached or has entered. They have little or no effect on non-localized cells. Radionuclides are essentially non-immunogenic.

With respect to the use of radiolabeled conjugates in conjunction with the present invention, binding molecules of the invention may be directly labeled (such as through iodination) or may be labeled indirectly through the use of a chelating agent as a tag moiety. As used herein, the phrases "indirect labeling" and "indirect labeling approach" both mean that a chelating agent is covalently attached to a binding molecule and at least one radionuclide is associated with the chelating agent. Such chelating agents are typically referred to as bifunctional chelating agents as they bind both the polypeptide and the radioisotope. Particularly preferred chelating agents comprise 1-isothiocycmatobenzyl-3-methyldiothelene triaminepentaacetic acid ("MX-DTPA") and cyclohexyl diethylenetriamine pentaacetic acid ("CHX-DTPA") derivatives. Other chelating agents comprise P-DOTA and EDTA derivatives. Particularly preferred radionuclides for indirect labeling include $^{111}$In and $^{90}$Y.

As used herein, the phrases "direct labeling" and "direct labeling approach" both mean that a radionuclide is covalently attached directly to a binding molecule (typically via an amino acid residue).

In yet another embodiment, Z is a pharmokinetic moiety. A pharmokinetic moiety is a moiety which improves the pharmokinetic properties of the binding molecule and allows the binding molecule to perform its intended function. Examples of pharmokinetic moieties include moieties which enhance solubility of the molecule (e.g., PEG, etc.), moieties which enhance transport of the molecule (e.g., agents which enhance the ability of the binding molecule to cross the blood brain barrier, cell membranes, etc.), moieties which enhance the half life of the molecule in a subject, or moeities that enhance other desirable properties of the molecule in a subject.

In another embodiment, the invention pertains, at least in part, to binding molecules of the formula (II):

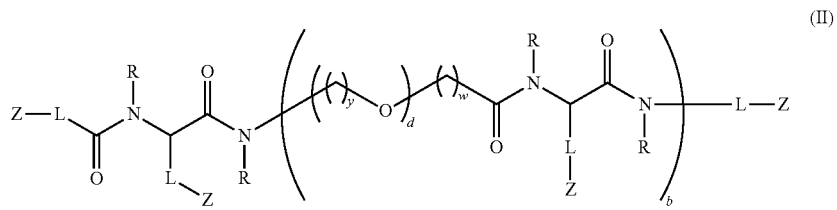

(II)

wherein
Ab is a polypeptide comprising at least one antigen binding site;
L is an independently selected linker moiety for each occurrence or B when Z is Ab;
B is a bridging moiety;
R is selected independently for each occurrence from the group consisting of alkyl, alkenyl, alkynyl, acyl, and hydrogen;
Z is an independently selected drug moiety, affinity moiety, tag moiety, pharmokinetic moeity, hydrogen, amino acid side chain moiety, or Ab for each occurrence;
w and y are each independently selected for each occurrence from the group consisting of 1, 2, 3, 4, and 5;
b and d are each independently selected for each occurrence from integers greater than 1, provided that at least one Z is Ab, and pharmaceutically acceptable salts, esters, and prodrugs thereof.

In a further embodiment, the binding molecules of the invention are compounds of formula (IIa), (IIb), (IIc) or (IId):

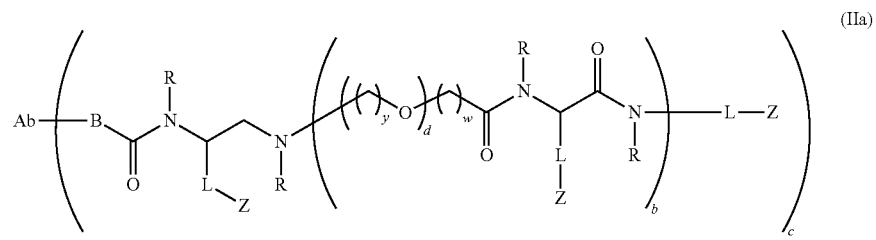

(IIa)

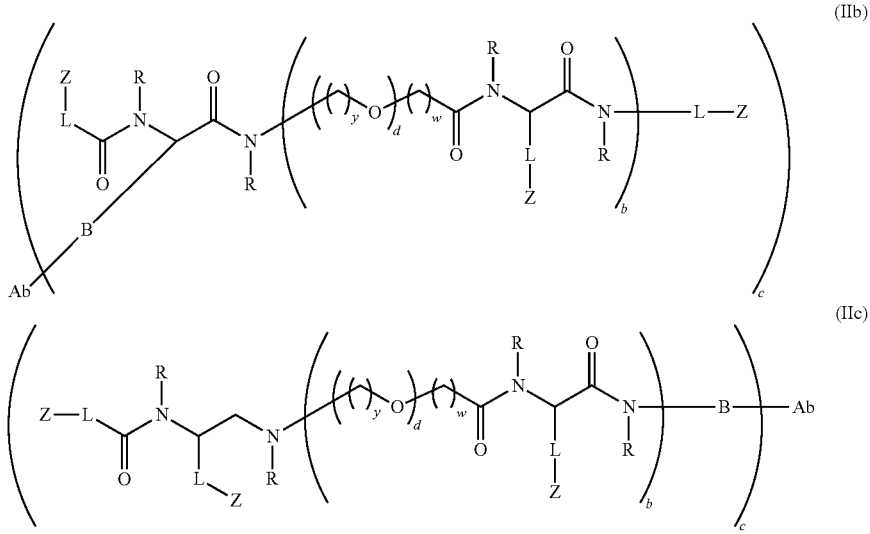

wherein

R is selected independently for each occurrence from the group consisting of alkyl, alkenyl, alkynyl, acyl, and hydrogen;

L is an independently selected linker moiety for each occurrence;

Z is an independently selected drug moiety, affinity moiety, tag moiety, hydrogen, or an amino acid side chain moiety for each occurrence;

Ab is a polypeptide comprising at least one antigen binding site;

B is a bridging moiety;

w and y are each independently selected for each occurrence from the group consisting of 1, 2, 3, 4, and 5;

b, c, and d are each independently selected for each occurrence from integers greater than 1.

In a further embodiment, the binding molecule of the invention is of the formula:

ment, c is selected such that the polypeptide comprising the antigen binding site is a properly folded polypeptide.

In a further embodiment, y is 2. In another further embodiment, d is 1, 2, or 3 and w is 1 or 2. In a preferred embodiment, y, d, and w are selected such that the resulting binding molecule is able to perform its intended function. In another embodiment, y, d, and w are selected such that the resulting moiety is hydrophilic or water soluble. In a further embodiment, the carbons comprising the y, d, and w repeating units are optionally substituted in a manner that allows them to perform their intended function. Examples of substituents in hydroxyl, halogen (e.g., fluoro), cyano, alkyl, etc.

In another embodiment, R is alkyl or hydrogen. In another further embodiment, R is lower alkyl, e.g., methyl, ethyl, propyl or butyl.

In another embodiment, Z is the side chain of a natural or unnatural amino acid. In certain embodiments, Z may be a proline side chain and linked to an adjacent R group to form

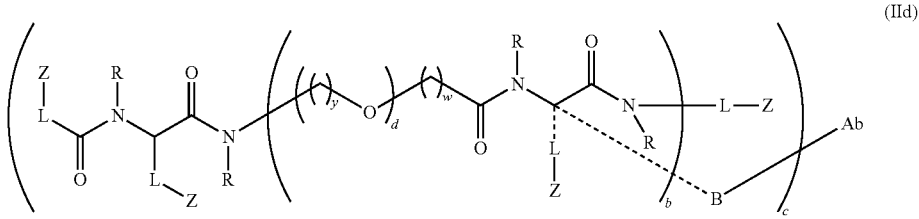

wherein L, Z, R, b, c, d, w, y, Ab, B, L, R, and Z are as described above, and wherein the dashed lines indicate for one occurrence for each c, the dashed line is a covalent bond to B-Ab, for the remainder of occurrences for each c, the dashed line is a covalent bond to L-Z.

A particular polypeptide comprising an antigen binding site of the invention may comprise 1, 2, 3, 4, 5, 6, 7, 8, 9, 10, 11, 12, etc. bridging moieties. The bridging moieties (e.g., the portion of the molecule encompassed by c) may be attached at different sites of the polypeptide comprising an antigen binding site of the invention.

For example, c may be an integer from 1 to about 100, 1 to about 50, 1 to about 25 or 1 to about 10. In a further embodia ring. Examples of side chains include, for example, those of alanine, cysteine, aspartic acid, glutamic acid, phenylalanine, glycine, histidine, iso leucine, lysine, leucine, methionine, asparagine, proline, glutamine, arginine, serine, threonine, valine, tryptophan, and tyrosine.

The term "unnatural amino acid" refers to any derivative of a natural amino acid including D forms, and α- and β-amino acid derivatives. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according to the invention (common abbreviations in parentheses): β-alanine (β-ALA), γ-aminobutyric acid (GABA), 2-aminobutyric acid (2-Abu), afl-dehydro-2-aminobutyric acid (8-AU), 1-aminocyclopropane-1-carboxylic acid (ACPC), aminoisobutyric acid (Aib), 2-amino-thiazoline-4-carboxylic acid, 5-aminovaleric acid (5-Ava), 6-aminohexanoic acid (6-Ahx), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid(4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-NH$_2$-Phe), biphenylalanine (Bip), para-bromophenylalanine (4-Br-Phe), ortho-chlorophenylalanine] (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), 2,3-diaminopropionic acid (Dpr), 2,4-diaminobutyric acid (Dbu), 3,4-dichlorophenylalanine (3,4-Cl$_2$-Phe), 3,4-difluororphenylalanine (3,4-F$_2$-Phe), 3,5-diiodotyrosine (3,5-I$_2$-Tyr), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), 5-hydroxytryptophan (5-OH-Trp), hydroxyproline (Hyp), para-iodophenylalanine (4-I-Phe), 3-iodotyrosine (3-I-Tyr), indoline-2-carboxylic acid (Idc), isonipecotic acid (Inp), meta-methyltyrosine (3-Me-Tyr), 1-naphthylalanine (1-Nal), 2-naphthylalanine (2-Nal), para-nitrophenylalanine (4-NO$_2$-Phe), 3-nitrotyrosine (3-NO$_2$-Tyr), norleucine (Nle), norvaline (Nva), ornithine (Orn), ortho-phosphotyrosine (H$_2$PO$_3$-Tyr), octahydroindole-2-carboxylic acid (Oic), penicillamine (Pen), pentafluorophenylalanine (F$_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), and thiazolidine-4-carboxylic acid (thioproline, Th).

The term "linking moiety" include moieties which are capable of linking the Z moiety to the remainder of the binding molecule. In certain embodiments where Z is hydrogen or an amino acid side chain, the linking moiety may be a covalent bond. The linking moiety may be selected such that it is cleavable or non-cleavable. Uncleavable linkers generally have high systemic stability, but may also have unfavorable pharmacokinetics. It should be noted that for certain Z moieties, such as affinity moieties and tag moieties, non-cleavable linking moieties may be preferred. In certain embodiments, branching moieties may comprise one or more linking moieties.

For drug moieties, the extracellular stability and intracellular cleavage mechanism of the linker need to be considered in the context of the potency of the drug moiety that is delivered when selecting a cleavable linker. In certain embodiments, the linker is selected such that the released drug sustains its beneficial actions with reduced side effects (as compared to administering the drug with out the binding molecule of the invention).

The cleavable linkers may be cleaved by externally applied stimulus, such as heat or light. Preferably, the cleavable linkers may be cleaved by biologically supplied stimulus (e.g., in vivo), such as a drop of pH, enzymatic cleavage or a change in redox potential.

In redox-triggered release, the cleavable linker may be cleaved in environments with a lower redox potential, such the cytoplasm and other regions with higher concentrations of molecules with free sulfhydryl groups. Examples of linkers that may be cleaved due to a change in redox potential include disulfides.

In acid triggered hydrolysis, a decrease in pH triggers the release of the cargo into the target cell. The decrease in pH is implicated in many physiological and pathological processes, such as endosome trafficking, tumor growth, inflammation, and myocardial ischemia. The pH drops from a physiological 7.4 to 5-6 in endosomes or 4-5 in lysosomes. Examples of acid sensitive linkers which may be used to target lysosomes or endosomes of cancer cells, include the following acetals, ketals, orthoesters, hydrazones, trityls, cis-aconityl, thiocarbamoyl, etc.

The binding molecules of the invention can be designed with peptide linkers that are sensitive to, for example, lysosomal or tumor-associated enzymes. Examples of linkers that can be cleaved enzymatically include, but are not limited to, peptides and esters.

In a further embodiment, L may be of the formula (VII):

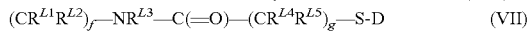

wherein
R$^{L1}$, R$^{L2}$, R$^{L3}$, R$^{L4}$, and R$^{L5}$ are each independently alkyl, alkenyl, alkynyl, acyl, or hydrogen;
f and g are each independently selected for each occurrence from the group consisting of 0, 1, 2, 3, 4, 5, and 6; and
D is a drug attachment moiety.

In a further embodiment, R$^{L1}$, R$^{L2}$, R$^{L3}$, R$^{L4}$, and R$^{L5}$ are each independently hydrogen or methyl. In another further embodiment, f is 3 and each of R$^{L1}$ and R$^{L2}$ are hydrogen. In another further embodiment, R$^{L3}$ is hydrogen.

The term "drug attachment moiety" may include any moiety which is capable of linking L to the Z moiety. For example, the drug attachment moiety may be a chain of 0-20 covalently linked, optionally substituted atoms. For example, the drug attachment moiety is comprised of alkyl, carbonyl, ester, amide, ether, disulfide, or other moieties. In a further embodiment, D comprises a moiety of the formula (VIII):

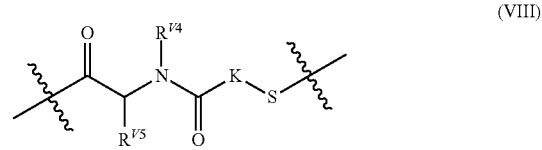

wherein
R$^{V4}$ and R$^{V5}$ are each hydrogen or lower alkyl; and
K is an alkyl or cycloalkyl linker comprising 1 to 10 carbon atoms.

In another embodiment, D comprises a moiety of the formula (IX):

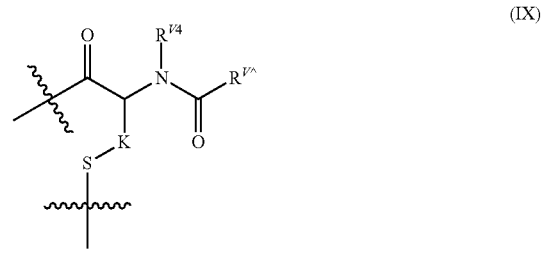

wherein $R^{V4}$ is hydrogen or lower alkyl;

$R^{V6}$ is alkyl comprising 1 to 10 carbon atoms; and

K is an alkyl or cycloalkyl linker comprising 1 to 10 carbon atoms.

In a further embodiment, $R^{V4}$ and $R^{V5}$ are each methyl. In a further embodiment, K comprises 1, 2, or 3 carbon atoms. In a further embodiment, K is $-(CH_2)_{0-3}-$.

In each of formulae (VIII) and (IX), S represents a sulfur atom and a covalent linkage to L. The carbonyl group is linked to the Z group.

The term "bridging moiety" includes moieties which link Ab to the remainder of the molecule. Branching moieties (M) may comprise one or more bridging moieties. The bridging molecule may be attached to the antibody through a disulfide linkage, an ester, an amide, ether, thioether, or peptide linkage. The bridging moiety may comprise an optionally substituted chain of covalently atoms (which may be straight chain, cyclic, or branched.) In one embodiment, the bridging moiety comprises about 0 to about 50 carbon, oxygen, nitrogen, and sulfur atoms, optionally substituted with hydrogens or other substituents which allow the compound of the invention to perform its intended function. The bridging molecule may be formed by the reaction of an attachment moiety with a binding molecule of the invention. Examples of bridging moieties include hydrazones, semicarbazones, and oximes.

In one embodiment, the bridging moiety is attached to the binding molecule of the invention through a disulfide linkage, e.g., through a cysteine residue. In one embodiment, the cysteine residue with which the disulfide linkage is formed is an exterior cysteine (e.g., a cysteine which does not form a disulfide bridge in the unmodified form of the polypeptide. In another embodiment, the bridging moiety is linked to a cysteine which does form disulfide bridges in the unmodified form of the polypeptide. In certain embodiments, the bridging moiety is linked to the polypeptide by cleaving one or more disulfide bonds in the polypeptide. The bridging moiety may also comprise urea, thioesters, etc. functional groups.

In other embodiments, the bridging moieties are attached to the binding molecules through carboxylate or amino groups of the polypeptide.

In another embodiment, the invention pertains to a bridging composition of the formula (III):

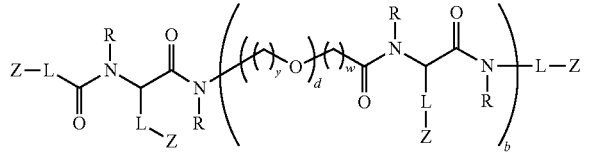

(III)

wherein

L is an independently selected linker moiety for each occurrence or B when Z is an attachment moiety;

B is a bridging moiety;

R is selected independently for each occurrence from the group consisting of alkyl, alkenyl, alkynyl, acyl, and hydrogen;

Z is an independently selected drug moiety, affinity moiety, tag moiety, hydrogen, amino acid side chain moiety, or an attachment moiety for each occurrence;

w and y are each independently selected for each occurrence from the group consisting of 1, 2, 3, 4, and 5;

b and d are each independently selected for each occurrence from integers greater than 1, provided that at least one Z is an attachment moiety, and provided that if only one Z is an attachment moiety, then each remaining Z is not a maytansinoid, and pharmaceutically acceptable salts, esters, and prodrugs thereof.

The term "attachment moiety" includes moieties which allow for the covalent attachment of the bridging composition of the invention to a polypeptide. The attachment moiety may comprise, for example, a covalent chain of 1-60 carbon, oxygen, nitrogen, sulfur atoms, optionally substituted with hydrogen atoms and other substituents which allow the bridging composition to perform its intended function. The attachment moiety may comprise peptide, ester, alkyl, alkenyl, alkynyl, aryl, ether, thioether, etc. functional groups. Preferably, the attachment moiety is selected such that it is capable of reacting with a reactive functional group on a polypeptide comprising at least one antigen binding site, to form a binding molecule of the invention. Examples of attachment moieties include, for example, amino, carboxylate, and thiol attachment moieties.

Amino attachment moieties include moieties which react with amino groups on a polypeptide, such that a binding molecule is formed. Amino attachment moieties are known in the art. Examples of amino attachment moieties include, activated carbamides (e.g., which may react with an amino group on Ab to form a urea bridging moiety), aldehydes (e.g., which may react with amino groups on Ab to form a reductive alkylation product), and activated isocyanates (which may react with an amino group on Ab to from a urea bridging moiety). Examples of amino bridging moieties include, but are not limited to, N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl, or 3-carboxy-4-nitrophenyl moiety.

In one embodiment, the amino attachment moiety is of the formula (X):

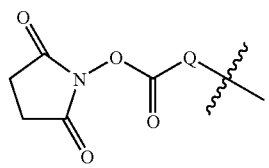

(X)

wherein

Q is a spacer or a covalent bond.

Carboxylate attachment moieties include moieties which react with carboxylate groups on a polypeptide, such that a binding molecule of the invention is formed. Carboxylate attachment moieties are known in the art. Examples of carboxylate attachment moieties include, but are not limited to activated ester intermediates and activated carbonyl intermediates, which may react with a COOH group on Ab to form a ester, thioester, or amide bridging moiety.

Thiol attachment moieties include moieties which react with thiol groups present on a polypeptide, such that a binding molecule of the invention is formed. Thiol attachment moieties are known in the art. Examples of thiol linking groups include activated acyl groups (which may react with a sulfhydryl on Ab to form a thioester bridging moiety), activated alkyl groups (which may react with a sulfhydryl on Ab to form a thioester bridging moiety), Michael acceptors such as maleimide or acrylic groups (which may react with a sulfhydryl on Ab to form a Michael-type addition product bridging moiety), groups which react with sulfhydryl groups via redox reactions, activated di-sulfide groups (which may react with a sulfhydryl group on Ab to form, for example, a disulfide bridging moiety). Other thiol attachment moieties include acrylamides, alpha-iodoacetamides, and cyclopropan-1,1-dicarbonyl compounds. In addition, the thiol attachment moiety may comprise a moiety which modifies the thiol to form another reactive species to which the bridging composition can be attached to form a binding protein of the invention.

In another embodiment, the thiol attachment moiety is of the formula (XI):

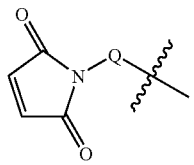

(XI)

wherein

Q is a spacer or a covalent bond.

The spacer, Q, is a covalent bond or a covalent chain of atoms which may contain one or more aminoacid residues. It may also comprise 0-60 carbon, oxygen, sulfur or nitrogen atoms optionally substituted with hydrogen or other substituents which allow the resulting binding molecule to perform its intended function. In one embodiment, Q comprises an alkyl, alkenyl, alkynyl, ester, ether, carbonyl, or amide moiety.

In another embodiment, the thiol is converted into a reactive group, such as a reactive carbonyl group, such as a ketone or aldehyde. The attachment moiety is then reacted with the ketone or aldehyde to form the bridging moiety. Examples of carbonyl reactive attachment moieties include, but are not limited to, hydrazines, hydrazides, O-substituted hydroxylamines, alpha-beta-unsaturated ketones, and $H_2C-CH-CO-NH-NH_2$. Other examples of attachment moieties and methods for modifying thiol moieties which can be used to form binding proteins of the invention are described Pratt, M. L. et al. J Am Chem. Soc. 2003 May 21; 125(20):6149-59; and Saxon, E. Science. 2000 Mar. 17; 287(5460):2007-10.

Variable and constant region domains can be obtained from any source and be incorporated into a binding molecule of the invention. To clone antibodies, mRNA can be isolated from hybridoma, spleen, or lymph cells, reverse transcribed into DNA, and antibody genes amplified by PCR. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250); or based on known variable region framework amino acid sequences from the Kabat (Kabat et al. 1991. Sequences of Proteins of Immunological Interest. Bethesda, Md.:JS Dep. Health Hum. Serv. 5th ed.) or the V-base databases (e.g., Orlandi et al. 1989. Proc. Natl. Acad. Sci. USA 86:3833; Sblattero et al. 1998. Immunotechnology 3:271; or Krebber et al. 1997. J. Immunol. Methods 201:35). Constant region domains can be selected having a particular effector function (or lacking a particular effector function) or with a particular modification to reduce immunogenicity. Variable and constant domains can be cloned, e.g., using the polymerase chain reaction and primers which are selected to amplify the domain of interest. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270).

Alternatively, V domains can be obtained from libraries of V gene sequences from an animal of choice. Libraries expressing random combinations of domains, e.g., VH and VL domains, can be screened with a desired antigen to identify elements which have desired binding characteristics. Methods of such screening are well known in the art. For example, antibody gene repertoires can be cloned into a X bacteriophage expression vector (Huse, W D et al. 1989. Science 2476:1275). In addition, cells (Boder and Wittrup. 1997. Nat. Biotechnol. 15:553; Daugtherty, P. et al. 2000. J. Immunol. Methods. 243:211; Francisco et al. 1994. Proc. Natl. Acad. Sci. USA 90:10444; Georgiou et al. 1997. Nature Biotechnology 15:29) or viruses (e.g., Hoogenboom, H R. 1998 Immunotechnology 4:1 Winter et al. 1994. Annu. Rev. Immunol. 12:433; Griffiths, A D. 1998. Curr. Opin. Biotechnol. 9:102) expressing antibodies on their surface can be screened. Ribosomal display can also be used to screen antibody libraries (Hanes J., et al. 1998. Proc. Natl. Acad. Sci. USA 95:14130; Hanes, J. and Pluckthun. 1999. Curr. Top. Microbiol. Immunol. 243:107; He, M. and Taussig. 1997. Nucleic Acids Research 25:5132):

Preferred libraries for screening are human V gene libraries. VL and VH domains from a non-human source may also be used. In one embodiment, such non-human V domains can be altered to reduce their immunogenicity using art recognized techniques.

Libraries can be naïve, from immunized subjects, or semisynthetic (Hoogenboom, H. R. and Winter. 1992. J. Mol. Biol. 227:381; Griffiths, A D, et al. EMBO J. 13:3245; de Kruif, J. et al. 1995. J. Mol. Biol. 248:97; Barbas, C. F., et al. 1992. Proc. Natl. Acad. Sci. USA 89:4457).

In addition, the sequences of many antibody V and C domains are known and such domains can be synthesized using methods well known in the art.

In one embodiment, mutations can be made to immunoglobulin domains to create a library of nucleic acid molecules having greater heterogeneity (Thompson, J., et al. 1996. J. Mol. Biol. 256:77; Lamminmaki, U. et al. 1999. J. Mol. Biol. 291:589; Caldwell, R. C. and Joyce G F. 1992. PCR Methods Appl. 2:28; Caldwell R C and Joyce G F. 1994. PCR Methods Appl. 3:S136. Standard screening procedures can be used to select high affinity variants. In another embodiment, changes to VH and VL sequences can be made to increase antibody avidity, e.g., using information obtained from crystal structures using techniques known in the art.

In one embodiment, a binding molecule of the invention comprises an immunoglobulin heavy chain having deletion or substitution of at least one amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other preferred embodiments may comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

In another embodiment, mutations to naturally occurring hinge regions can be made. Such modifications to the constant region in accordance with the instant invention may easily be made using well known biochemical or molecular engineering techniques well within the skill of the art.

In one embodiment, antigen binding molecules of the invention comprise modified constant regions wherein one or more domains are partially or entirely deleted ("domain deleted antibodies"). In especially preferred embodiments compatible modified antibodies will comprise domain deleted constructs or variants wherein the entire CH2 domain has been removed. A variety of modified antibody constructs are described in more detail below.

In one embodiment, the antigen binding molecules of the invention comprise minibodies. Minibodies are dimeric molecules made up of two polypeptide chains each comprising an ScFv molecule (a single polypeptide comprising one or more antigen binding sites, e.g., a VL domain linked by a flexible linker to a VH domain fused to a CH3 domain via a connecting peptide. ScFv molecules can be constructed in a VH-linker-VL orientation or VL-linker-VH orientation.

Methods of making single chain antibodies are well known in the art, e.g., Ho et al. 1989. Gene 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837.

Minibodies can be made by constructing an ScFv component and connecting peptide-CH3 component using methods described in the art (see, e.g., U.S. Pat. No. 5,837,821 or WO 94/09817A1). These components can be isolated from separate plasmids as restriction fragments and then ligated and recloned into an appropriate vector. Appropriate assembly can be verified by restriction digestion and DNA sequence analysis.

In another embodiment, the antigen binding molecules of the invention comprise CH2 domain deleted antibodies. Domain deleted constructs can be derived from a vector (e.g., from BiogenIDEC Pharmaceuticals, San Diego) encoding an $IgG_1$ human constant domain (see, e.g., WO 02/060955A2 and WO02/096948A2). Essentially, the vectors can be engineered to delete the CH2 domain and provide a modified vector expressing a domain deleted IgG, constant region in which the CH3 domain is fused to a hinge region or to a CH1 domain via a connecting peptide. These constructs exhibit a number of properties that make them particularly attractive modified antibodies.

Besides the deletion of whole constant region domains, it will be appreciated that the antigen binding molecules of the present invention can be engineered to partially delete or substitute of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement C1Q binding). Such partial deletions of the constant regions may improve selected characteristics of the antigen binding molecule (serum half-life) while leaving other desirable functions associated with the subject constant region domain intact.

Creation of a CH2 domain deleted version can be accomplished by way of overlapping PCR mutagenesis. The gamma 1 constant domain begins with a plasmid encoded Nhe I site with is in translational reading frame with the immunoglobulin sequence. A 5' PCR primer was constructed encoding the Nhe I site as well as sequence immediately downstream. A 3' PCR primer mate was constructed such that it anneals with the 3' end to the immunoglobulin hinge region and encodes in frame the first several amino acids of the gamma 1 CH3 domain. A second PCR primer pair consisted of the reverse complement of the 3' PCR primer from the first pair (above) as the 5' primer and a 3' primer that anneals at a loci spanning the BsrG I restriction site within the CH3 domain. Following each PCR amplification, the resultant products were utilized as template with the Nhe I and BsrG 15' and 3', respectively primers. The amplified product was then cloned back into N5KG1 to create the plasmid N5KG1ΔCH$_2$. This construction places the intact CH3 domain immediately downstream and in frame with the intact hinge region. A similar procedure can be used to create a domain deleted construct in which the CH3 domain is immediately downstream of a connecting peptide. For example, a domain deleted version of the C2B8 antibody was created in this manner as described in U.S. Pat. Nos. 5,648,267 and 5,736,137 each of which is incorporated herein by reference.

In one embodiment, tetravalent domain-deleted antibodies can be produced by combining a DNA sequence encoding a domain deleted antibody with a ScFv molecule. For example, in one embodiment, these sequences are combined such that the ScFv molecule is linked at its N-terminus to the CH3 domain of the domain deleted antibody via a flexible linker (e.g., a gly/ser linker such as (Gly4Ser)$_3$.

In another embodiment a tetravalent antibody can be made by fusing an ScFv molecule to a connecting peptide, which is fused to a CH1 domain to construct an ScFv-Fab tetravalent molecule. (Coloma and Morrison. 1997. Nature Biotechnology. 15:159; WO 95/09917).

In another embodiment, the antigen binding molecules of the invention may comprise diabodies as the polypeptide comprising an antigen binding site. Diabodies are similar to scFv molecules, but usually have a short (less than 10 and preferably 1-5) amino acid residue linker connecting both V-domains, such that the VL and VH domains on the same polypeptide chain can not interact. Instead, the VL and VH domain of one polypeptide chain interact with the VH and VL domain (respectively) on a second polypeptide chain (WO 02/02781).

Other forms of modified antibodies are also within the scope of polypeptides comprising antigen binding sites (e.g., WO 02/02781 A1; U.S. Pat. Nos. 5,959,083; 6,476,198 B1; US 2002/0103345 A1; WO 00/06605; Byrn et al. 1990. Nature. 344:667-70; Chamow and Ashikenazi. 1996. Trends Biotechnol. 14:52).

Following manipulation of the isolated genetic material to provide polypeptide comprising antigen binding sites of the invention as set forth above, the genes are typically inserted in an expression vector for introduction into host cells that may be used to produce the desired quantity of modified antibody that, in turn, provides the polypeptide portion of the antigen binding molecule.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Exemplary vectors include those taught in U.S. Pat. No. 6,159,730 or 6,413,777 or US 2003 0157641 A1). Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

In one embodiment, an inducible expression system can be employed.

Additional elements may also be needed for optimal synthesis of mRNA. These elements may include signal sequences, splice signals, as well as transcriptional promoters, enhancers, and termination signals.

In one embodiment, a secretion signal, e.g., any one of several well characterized bacterial leader peptides (e.g., pelB, phoA, or ompA), can be fused in-frame to the N terminus of a polypeptide of the invention to obtain optimal secretion of the polypeptide. (Lei et al. 1988 Nature 331:543; Better et al. Science 1988. 240:1041; Mullinax et al., 1990. Proc. Natl. Acad. Sci. USA 87:8095).

In one embodiment, a vector can be used which comprises a nucleic acid sequence encoding a peptide linker. In another embodiment, it might be desirable to first assemble the desired coding sequences (e.g., secretion signal, VL, linker peptide, VH, etc.) into a single sequence, for example, by PCR amplification using overlapping primers, followed by ligation into a plasmid or other vector.

In particularly preferred embodiments the cloned variable region genes are inserted into an expression vector along with the heavy and light chain constant region genes (preferably human) modified as discussed above. Preferably, this is effected using a proprietary expression vector of BiogenIDEC, Inc., referred to as NEOSPLA. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. As seen in the examples below, this vector has been found to result in very high level expression of antibodies upon incorporation of variable and constant region genes, transfection in CHO cells, followed by selection in G418 containing medium and methotrexate amplification. This vector system is substantially disclosed in commonly assigned U.S. Pat. Nos. 5,736,137 and 5,658,570, each of which is incorporated by reference in its entirety herein. This system provides for high expression levels, e.g., >30 pg/cell/day.

In other preferred embodiments the polypeptides of the invention of the instant invention may be expressed using polycistronic constructs such as those disclosed in U.S. provisional application No. 60/331,481 filed Nov. 16, 2001 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is also incorporated herein. Those skilled in the art will appreciate that such expression systems may be used to effectively produce the full range of polypeptides disclosed in the instant application.

More generally, once the vector or DNA sequence encoding a monomeric subunit of the polypeptide (e.g. a modified antibody) has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

As used herein, the term "transformation" shall be used in a broad sense to refer to any introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CV1 (monkey kidney line), COS (a derivative of CV1 with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature.

In another embodiment, a host cell is a prokaryotic cell, e.g., a strain which allows the formation of disulfide bonds (Derman, A I, et al. 1993. Science. 262:1744; Bessette, P H. Etal. 1999. Proc. Natl. Acad. Sci. USA 96:13703).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g. after preferential biosynthesis of a modified hinge region polypeptide or prior to or subsequent to the HIC chromatography step described herein.

Genes encoding the polypeptide of the invention can also be expressed non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules. Where tetravalent forms of antibodies are desired, the subunits will then self-assemble into tetravalent antibodies (WO02/096948A2).

In addition to prokaryates, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan.

In one embodiment, the invention pertains to a method for treating a subject suffering from a disorder that would benefit from treatment with a binding molecule, by administering to the subject an effective amount of a binding molecule of the invention.

The binding molecules of the invention can be used for diagnostic or therapeutic purposes. Preferred embodiments of the present invention provide molecules, compositions, kits and methods for the diagnosis and/or treatment of disorders, e.g., neoplastic disorders in a mammalian subject in need of such treatment. Preferably, the subject is a human. The binding molecules of the instant invention will be useful in a number of different applications. For example, in one embodiment, the subject binding molecules may be useful for reducing or eliminating cells bearing an antigen recognized by a binding molecule of the invention.

In one embodiment, the invention pertains to a method for treat cancer. In one embodiment, the cancer has resulted in the formation of a tumor. In a further embodiment, the antigen binding molecules of the invention may be used to reduce tumor size, inhibiting tumor growth and/or prolonging the survival time of tumor-bearing animals. Accordingly, this invention also relates to a method of treating tumors in a human or other animal by administering to such human or animal an effective, non-toxic amount of binding molecules. One skilled in the art would be able, by routine experimentation, to determine what an effective, non-toxic amount of the binding molecules of the invention would be for the purpose of treating malignancies. For example, a therapeutically active amount of a binding molecule may vary according to factors such as the disease stage (e.g., stage I versus stage IV), age, sex, medical complications (e.g., immunosuppressed conditions or diseases), number and type of drug moieties on the molecule, and weight of the subject, and the ability of the antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10, milligrams per kilogram body weight per day.

In another embodiment, the subject is suffering, for example, from lymphoma, an autoimmune disorder or disease, an inflammatory disease or disorder, or another disease or disorder which can be treated using the binding molecules of the invention.

In a further embodiment, the invention pertains to a method, for example but not limited to, of treating a subject for colorectal cancer, by administering to the subject an effective amount of a binding molecule of the invention.

In another further embodiment, the invention pertains to, for example but not limited to, a method for treating a subject for pancreatic cancer, by administering to the subject an effective amount of binding molecule of the invention.

In another further embodiment, the invention pertains to, for example but not limited to, a method for treating a subject for acute myelogenous leukemia (AML), by administering to the subject an effective amount of binding molecule of the invention.

For purposes of clarification "mammal" refers to any animal classified as a mammal, including humans, domestic and farm animals, and zoo, sports, or pet animals, such as dogs, horses, cats, cows, etc. Preferably, the mammal is human.

"Treatment" refers to both therapeutic treatment and prophylactic or preventative measures. Those in need of treatment include those already with the disease or disorder as well as those in which the disease or disorder is to be prevented. Hence, the mammal may have been diagnosed as having the disease or disorder or may be predisposed or susceptible to the disease.

As discussed above, the binding molecules of the present invention may be specifically bind one or more tumor antigens or antigens associated with immune disorders. For example, for neoplastic disorders, the antigen binding site (i.e. the variable region or immunoreactive fragment or recombinant thereof) of the disclosed binding molecules may bind to a selected tumor associated antigen at the site of the malignancy. Similarly, in immune (including autoimmune) disorders the disclosed binding molecules may bind to selected markers on the offending cells. Given the number of reported antigens associated with neoplasias and immune disorders, and the number of related antibodies, those skilled in the art will appreciate that the presently disclosed polypeptides comprising an antigen binding site may therefore be derived from any one of a number of whole antibodies. More generally, polypeptides useful in the present invention may be obtained or derived from any antibody (including those previously reported in the literature) that reacts with an antigen or marker associated with the selected condition. Further, the parent or precursor antibody, or fragment thereof, used to generate the disclosed polypeptides may be murine, human, chimeric, humanized, non-human primate or primatized. Consequently, any of these types of antibodies modified in accordance with the teachings herein are compatible with the instant invention.

As used herein, "tumor associated antigens" means any antigen which is generally associated with tumor cells, i.e., occurring at the same or to a greater extent as compared with normal cells. More generally, tumor associated antigens comprise any antigen that provides for the localization of immunoreactive antibodies at a neoplastic cell irrespective of its expression on non-malignant cells. Such antigens may be relatively tumor specific and limited in their expression to the surface of malignant cells. Alternatively, such antigens may be found on both malignant and non-malignant cells. For example, CD20 is a pan B antigen that is found on the surface of both malignant and non-malignant B cells that has proved to be an extremely effective target for immunotherapeutic antibodies for the treatment of non-Hodgkin's lymphoma. In this respect, pan T cell antigens such as CD2, CD3, CD5, CD6 and CD7 also comprise tumor associated antigens within the meaning of the present invention. Still other exemplary tumor associated antigens comprise but not limited to MAGE-1, MAGE-3, MUC-1, HPV 16, HPV E6 & E7, TAG-72, CEA, L6-Antigen, CD19, CD22, CD33, CD37, CD52, HLA-DR, EGF Receptor and HER2 Receptor. In many cases immunoreactive antibodies for each of these antigens have been reported in the literature. Those skilled in the art will appreciate that each of these antibodies may serve as a precursor for polypeptides comprising antigen binding sites of the invention in accordance with the present invention.

The binding molecules of the present invention preferably associate with, and bind to, tumor or other cancer associated antigens as described above. Accordingly, as will be discussed in some detail below the polypeptides of the present invention comparing at least one antigen binding site may be derived, generated or fabricated from any one of a number of antibodies that react with tumor or cancer associated antigens. In an embodiments the polypeptides comprising at least one antigen binding site are modified or domain deleted antibodies that are derived using common genetic engineering techniques whereby at least a portion of one or more constant region domains are deleted or altered so as to provide the desired biochemical characteristics such as reduced serum half-life. More particularly, as will be exemplified below, one skilled in the art may readily isolate the genetic sequence corresponding to the variable and/or constant regions of the subject antibody and delete or alter the appropriate nucleotides to provide polypeptides of the invention for use as monomeric subunits in accordance with the instant invention. It will further be appreciated that compatible polypeptides of the invention may be expressed and produced on a clinical or commercial scale using well-established protocols.

Previously reported antibodies that react with tumor associated antigens may be altered as described herein to provide the polypeptides of the present invention comprising at least one antigen binding site. Exemplary antibodies that may be used to provide antigen binding regions for, generate or derive the disclosed polypeptides include, but are not limited to Y2B8 and C2B8 (Zevalin™ and Rituxan®, BiogenIDEC Pharmaceuticals Corp., San Diego), Lym 1 and Lym 2 (Techniclone), LL2 (Immunomedics Corp., New Jersey), HER2 (Herceptin®, Genentech Inc., South San Francisco), B1 (Bexxaro, Coulter Pharm., San Francisco), Campath® (Millennium Pharmaceuticals, Cambridge) MB1, BH3, B4, B72.3 (Cytogen Corp.), CC49 (National Cancer Institute) and 5E10 (University of Iowa). In preferred embodiments, the polypeptides of the present invention will bind to the same tumor associated antigens as the antibodies enumerated immediately above.

In general, the disclosed invention may be used to prophylactically or therapeutically treat any neoplasm comprising an antigenic marker that allows for the targeting of the cancerous cells by the binding molecule of the invention. Exemplary cancers that may be treated include, but are not limited to, prostate, gastric carcinomas such as colon, skin, breast, ovarian, lung and pancreatic. More particularly, the antibodies of the instant invention may be used to treat Kaposi's sarcoma, CNS neoplasias (capillary hemangioblastomas, meningiomas and cerebral metastases), melanoma, gastrointestinal and renal sarcomas, rhabdomyosarcoma, glioblastoma (preferably glioblastoma multiforme), leiomyosarcoma, retinoblastoma, papillary cystadenocarcinoma of the ovary, Wilm's tumor or small cell lung carcinoma. It will be appreciated that appropriate polypeptides may be derived for tumor associated antigens related to each of the forgoing neoplasias without undue experimentation in view of the instant disclosure.

Exemplary hematologic malignancies that are amenable to treatment with the disclosed invention include Hodgkins and non-Hodgkins lymphoma as well as leukemias, including ALL-L3 (Burkitt's type leukemia), chronic lymphocytic leukemia (CLL) and monocytic cell leukemias. It will be appreciated that the compounds and methods of the present invention are particularly effective in treating a variety of B-cell lymphomas, including low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention. In addition to the aforementioned neoplastic disorders, it will be appreciated that the disclosed invention may advantageously be used to treat additional malignancies bearing compatible tumor associated antigens.

In another embodiment, the invention pertains to compositions comprising a binding molecule of the invention and a pharmaceutically acceptable carrier.

Methods of preparing and administering the binding molecules of the invention to a subject are well known to or are readily determined by those skilled in the art. The route of administration of the antigen binding molecules of the invention may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1 M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating a binding molecule (e.g., a binding molecule by itself or in combination with other active agents) in the required amount in an appropriate solvent with one or a combination of ingredients enumerated herein, as required, followed by filtered sterilization. Generally, dispersions are prepared by incorporating the binding molecules into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338 each of which is incorporated herein by reference. Such articles of manufacture will preferably have labels or package inserts indicating that the associated compositions are useful for treating a subject suffering from, or predisposed to autoimmune or neoplastic disorders.

Effective doses of the compositions of the present invention, for the treatment of the above described conditions vary depending upon many different factors, including means of administration, target site, particular drug moiety, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

The dosage of the binding molecule of the invention can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly.

Binding molecules of the invention can be administered on multiple occasions. Intervals between single dosages can be weekly, monthly or yearly. Intervals can also be irregular as indicated by measuring a particular indicator in a subject. In some methods, dosage is adjusted to achieve a plasma polypeptide concentration of 1-1000 µg/ml and in some methods 25-300 µg/ml. Alternatively, binding molecules can be administered as a sustained release formulation, in which case less frequent administration is required. Dosage and frequency vary depending on the half-life of the binding molecule in the patient.

In therapeutic applications, a relatively high dosage (e.g., from about 1 to 400 mg/kg of binding molecule per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

Binding molecules can be administered by parenteral, topical, intravenous, oral, subcutaneous, intraarterial, intracranial, intraperitoneal, intranasal or intramuscular means for prophylactic and/or therapeutic treatment. The most typical route of administration of a binding molecule is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection or intravenous infusion are preferred for administration of antibody. In some methods, particular binding molecules are injected directly into the cranium. In some methods, binding molecules are administered as a sustained release composition or device, such as a Medipad™ device.

Binding molecules of the invention can optionally be administered in combination with other agents that are effective in treating the disorder or condition in need of treatment (e.g., prophylactic or therapeutic).

Effective single treatment dosages (i.e., therapeutically effective amounts) of $^{90}$Y-labeled binding molecules of the invention range from between about 5 and about 75 mCi, more preferably between about 10 and about 40 mCi. Effective single treatment non-marrow ablative dosages of $^{131}$I-labeled binding molecules range from between about 5 and about 70 mCi, more preferably between about 5 and about 40 mCi. Effective single treatment ablative dosages (i.e., may require autologous bone marrow transplantation) of $^{131}$I-labeled binding molecules range from between about 30 and about 600 mCi, more preferably between about 50 and less than about 500 mCi. Imaging criteria for, e.g., the $^{111}$In label, are typically less than about 5 mCi.

While a great deal of clinical experience has been gained with $^{131}$I and $^{90}$Y, other radiolabels are known in the art and have been used for similar purposes. Still other radioisotopes are used for imaging. For example, additional radioisotopes which are compatible with the scope of the instant invention include, but are not limited to, $^{123}$I, $^{125}$I, $^{32}$P, $^{57}$Co, $^{64}$Cu, $^{67}$Cu, $^{77}$Br, $^{81}$Rb, $^{81}$Kr, $^{87}$Sr, $^{113}$In, $^{127}$Cs, $^{129}$Cs, $^{132}$I, $^{197}$Hg, $^{203}$Pb, $^{206}$Bi, $^{77}$Lu, $^{186}$Re, $^{212}$Pb, $^{212}$Bi, $^{47}$Sc, $^{105}$Rh, $^{109}$Pd, $^{153}$Sm, $^{188}$Re, $^{199}$Au, $^{225}$Ac, $^{211}$At, and $^{213}$Bi. In this respect alpha, gamma and beta emitters are all compatible with in the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include $^{125}$, I $^{123}$I, $^{99}$Tc, $^{43}$K, $^{52}$Fe, $^{67}$Ga, $^{68}$Ga, as well as $^{111}$In. Binding molecules may also be labeled with a variety of radionuclides for potential use in targeted immunotherapy (Peirersz et al. *Immunol. Cell Biol.* 65: 111-125 (1987)). These radionuclides include $^{188}$Re and $^{186}$Re as well as $^{199}$Au and $^{67}$Cu to a lesser extent. U.S. Pat. No. 5,460,785 provides additional data regarding such radioisotopes and is incorporated herein by reference.

It will further be appreciated that the binding molecules of the instant invention may be used in conjunction or combination with any chemotherapeutic agent or agents (e.g. to provide a combined therapeutic regimen) that eliminates, reduces, inhibits or controls the growth of neoplastic cells in vivo. With respect to these aspects of the invention, exemplary chemotherapeutic agents that are compatible with the instant invention include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present invention. In MOPP-resistant patients, ABVD (e.g., adriamycin, bleomycin, vinblastine and dacarbazine), ChlVPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. Arnold S. Freedman and Lee M. Nadler, *Malignant Lymphomas*, in HARRISON'S PRINCIPLES OF INTERNAL MEDICINE 1774-1788 (Kurt J. Isselbacher et al., eds., 13$^{th}$ ed. 1994) and V. T. DeVita et al., (1997) and the references cited therein for standard dosing and scheduling. These therapies can be used unchanged, or altered as needed for a particular patient, in combination with one or more antigen binding molecules of the invention as described herein.

Additional regimens that are useful in the context of the present invention include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), Pro-MACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). Those skilled in the art will readily be able to determine standard dosages and scheduling for each of these regimens. CHOP has also been combined with bleomycin, methotrexate, procarbazine, nitrogen mustard, cytosine arabinoside and etoposide. Other compatible chemotherapeutic agents include, but are not limited to, 2-chlorodeoxyadenosine (2-CDA), 2'-deoxycoformycin and fludarabine.

For patients with intermediate- and high-grade NH, who fail to achieve remission or relapse, salvage therapy is used. Salvage therapies employ drugs such as cytosine arabinoside, cisplatin, etoposide and ifosfamide given alone or in combination. In relapsed or aggressive forms of certain neoplastic disorders the following protocols are often used: IMVP-16 (ifosfamide, methotrexate and etoposide), MIME (methylgag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well known dosing rates and schedules.

The amount of chemotherapeutic agent to be used in combination with the binding molecules of the instant invention may vary by subject or may be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., 9$^{th}$ ed. 1996).

As previously discussed, the binding molecules may be administered in a pharmaceutically effective amount for the in vivo treatment of mammalian disorders. In this regard, it will be appreciated that the disclosed antibodies will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of the binding molecule shall be held to mean an amount sufficient to achieve effective binding to an antigen and to achieve a benefit, e.g., to ameliorate symptoms of a disease or disorder or to detect a substance or a cell. In the case of tumor cells, the binding molecule will preferably be capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the binding molecule.

In keeping with the scope of the present disclosure, the binding molecules of the invention may be administered to a human or other animal in accordance with the aforementioned methods of treatment in an amount sufficient to produce a therapeutic or prophylactic effect. The binding molecules of the invention can be administered to such human or other animal in a conventional dosage form prepared by combining the binding molecules of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of polypeptides according to the present invention may prove to be particularly effective.

EXAMPLE

Synthesis of Bridging Compositions

The bridging compositions were synthesized by via an Fmoc strategy using the Applied Biosystems peptide synthesizer, Model 431A.

A. Solid Phase Synthesis of Bridging Composition 1.

Fmoc-Glycine pre-loaded HMP-resin (0.2 mmol, 290 mg) was placed into an ABI reaction vessel. Cartridges containing Fmoc-8-amino-3,6-dioxaoctanoic acid (1.0 mmol, 385.41 mg) and Fmoc-Lysine(Aloc)-OH were loaded onto the synthesizer and the machine was programmed using standard Fmoc protocols to assemble the peptide chain. The amino side chain of lysine was temporarily blocked with the allyloxy-carbonyl protecting group (Aloc) to allow selective deprotection before the final cleavage of the linker from the resin. The resin was removed from the reaction vessel and transferred to a 12-mL propylene filtration tube. The N-terminus of the peptidic linker was acetylated using acetic anhydride (2 mmol, 190 µL) and N,N-diisopropylethylamine (2 mmol, 348 µL) in N,N-dimethylformamide (5 mL) for 2 hours. The resin washed with N,N-dimethylformamide (4×5 mL) and dichloromethane (2×5 mL). To remove the Aloc group, the resin suspended in dichloromethane (5 mL) was treated with phenylsilane (8 mmol, 1.01 mL) and tetrakis (triphenylphosphine) palladium (0) (0.08 mmol, 92.4 mg). The reaction was run for 15 minutes at room temperature. This treatment was repeated three times. Then, the resin washed with N,N-dimethylformamide (4×5 mL), dichloromethane (4×5 mL), 5% piperidine in N,N-dimethylformamide (3×5 mL) and 1% ethanedithiol in N,N-dimethylformamide (3×5 mL). After, the resin washed with N,N-dimethylformamide (3×5mL), dichloromethane (3×5 mL),

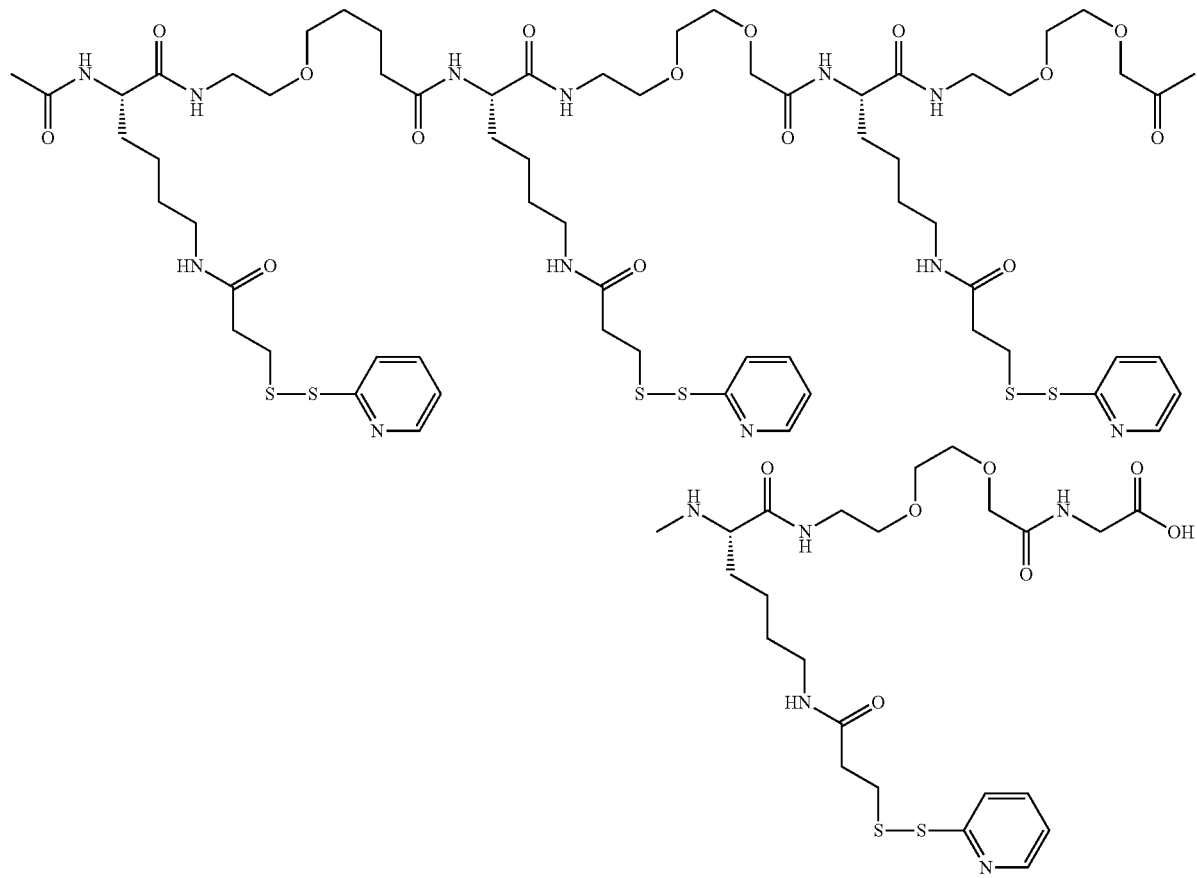

Bridging Composition 1 isopropyl alcohol (3×5 mL) and dichloromethane (4×5 mL). The resin was divided in two equals portions. One half of the resin was reacted with 3-(2-pyridyldithio) propionic acid N-hydroxysuccinimide ester (1.6 mmol, 500 mg) in N,N-dimethylformamide (4 mL) for 18 hrs. The resin washed with N,N-dimethylformamide (4×5 mL) and dichloromethane (2×5 mL). A sample of the resin (approximately 1.0 mg) was transferred to a test tube to run the Kaiser test to ensure completion of the reaction. The resin was dried using a vacuum pump for 18 hrs. The resulting product was cleaved form the resin with trifluoroacetic acid/water, 9/1 (5.0 mL) for two hours. The trifluoroacetic-acid-resin mixture was filtered to remove the resin. Trifluoroacetic acid was removed under reduced pressure. The crude product gave a major RP-HPLC peak (85%) that corresponded to MS, m/z 1,998.7.

reduced pressure. The crude product gave a major RP-HPLC peak (80%) that corresponded to MS, m/z 2,026.7.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. The contents of all references, patents, and patent applications cited throughout this application are hereby incorporated by reference.

The invention claimed is:

1. An isolated binding molecule of the formula (II):

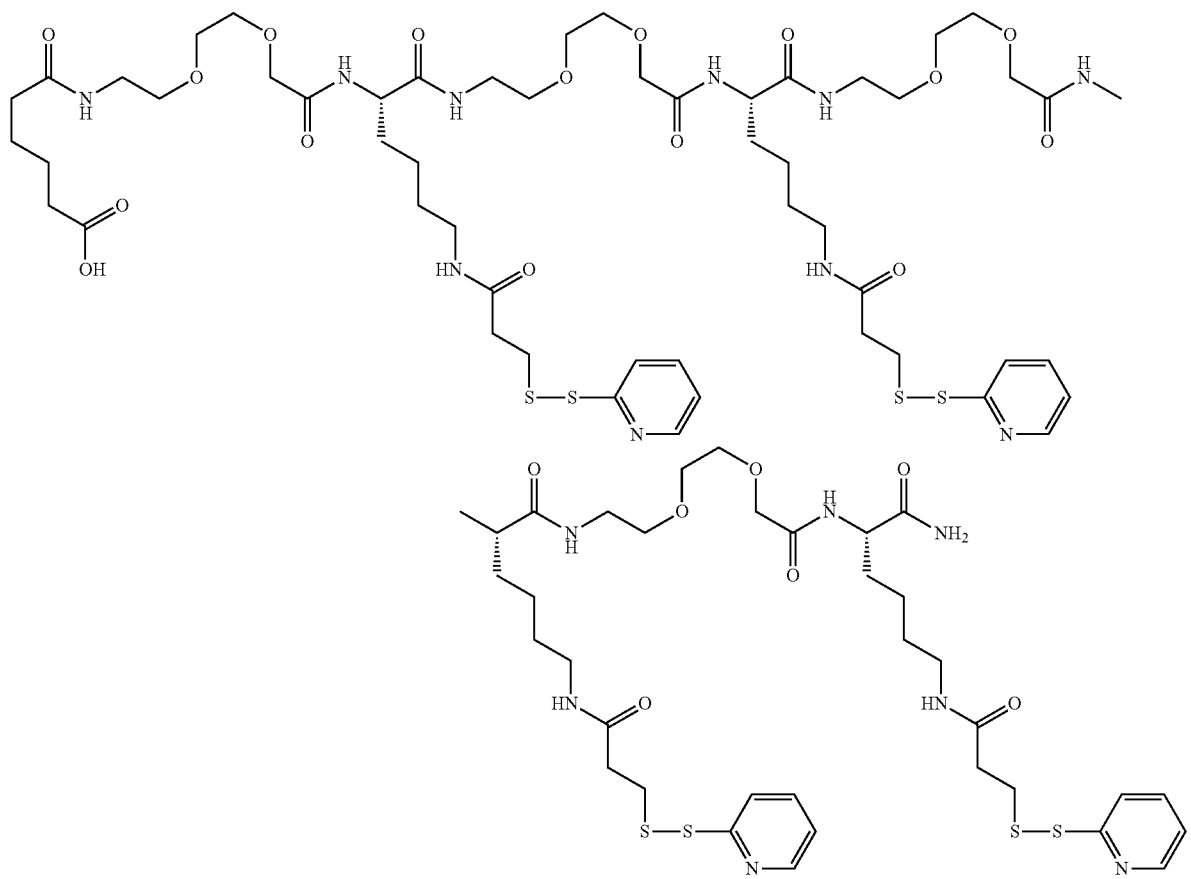

Bridging Composition 2

B. Solid Phase Synthesis of Bridging Composition 2.

Bridging Composition 2 was prepared with Rink Amide MBHA resin using the same machine-assisted protocol used for the synthesis of bridging composition 1. After the peptidic chain assembly was completed, the resin was transferred to a 12-mL polypropylene filtration tube. The resin was reacted with succinic anhydride (2.0 mmol, 200.0) in N,N-dimethylformamide (8 mL) for 24 hrs. The treatment was repeated twice until the Kaiser test was negative. The resin was dried using a vacuum pump for 18 hours. The product was cleaved form the resin with trifluoroacetic acid/water, 9/1 (5.0 mL) for two hours. The trifluoroacetic acid-resin mixture was filtered to remove the resin. Trifluoroacetic acid was removed under

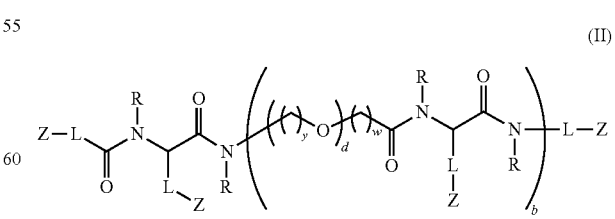

(II)

wherein
at least one Z is Ab, wherein Ab is a polypeptide comprising at least one antigen binding site;

L is an independently selected linker moiety for each occurrence or B when adjacent to a Z which is Ab;

B is a bridging moiety, wherein B is linked to Ab through a carboxylate or amino linkage;

R is selected independently for each occurrence from the group consisting of alkyl, alkenyl, alkynyl, acyl, and hydrogen;

Z is an independently selected drug moiety, affinity moiety, tag moiety, pharmokinetic moiety, hydrogen, amino acid side chain moiety, or Ab for each occurrence;

w and y are each independently selected for each occurrence from the group consisting of 1, 2, 3, 4, and 5;

b and d are each independently selected for each occurrence from integers greater than 1, and pharmaceutically acceptable salts, esters, and prodrugs thereof.

2. The binding molecule of claim 1, wherein at least one L is an attachment moiety.

3. The binding molecule of claim 1, wherein y is 2.

4. The binding molecule of claim 1, wherein d is 1, 2, or 3.

5. The binding molecule of claim 1, wherein w is 1 or 2.

6. The binding molecule of claim 1, wherein each R is independently alkyl or hydrogen.

7. The binding molecule of claim 1, wherein at least one Z is a drug moiety.

8. The binding molecule of claim 7, wherein said molecule comprises two or more drug moieties.

9. The binding molecule of claim 7, wherein said drug moiety is an anti-cancer, antibiotic, or anti-inflammatory agent.

10. The binding molecule of claim 9, wherein Z is an anticancer agent.

11. The binding molecule of claim 10, wherein Z is doxorubicin, etoposide, taxane, paclitaxel, fluorouracyl, mitomycin, camptothecin, a vinca alkaloid, geldanamycin, a gemcitabine, geldanamycin, epothilone, cephalostatin, tubulin inhibitors, proteasome inhibitors, neocarzinostatin, calicheamicin, maytansinoids, (RS)-cyclophophamide, 6-mercaptopurin, auristatin E, daunorubicin, or a derivative or analog thereof.

12. The binding molecule of claim 11, wherein Z is a maytansinoid of the formula (IV):

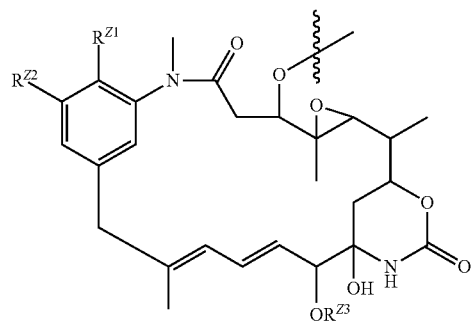

(IV)

wherein
$R^{Z1}$ is halogen or hydrogen; and
$R^{Z2}$ and $R^{Z3}$ are each hydrogen or lower alkyl.

13. The binding molecule of claim 12, wherein $R^{Z1}$ is chlorine and $R^{Z2}$ and $R^{Z3}$ are each methyl.

14. The binding molecule of claim 11, wherein Z is a taxane derivative of the formula (V):

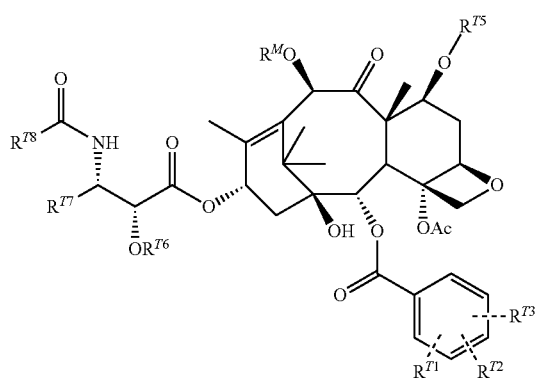

(V)

wherein:
$R^{T1}$, $R^{T2}$, and $R^{T3}$ and $R^{T3}$ are each independently hydrogen, an electron withdrawing group, or an electron donating group;

$R^{T4}$, $R^{T5}$, $R^{T6}$ are each independently a covalent bond to L, hydrogen, heterocyclic, an ester, an ether, a carbamate of the formula —$CONR^{T10}R^{T11}$, wherein $R^{T10}$ and $R^{T11}$ are each independently hydrogen, alkyl, alkenyl, alkynyl, acyl or aryl, provided that one of $R^{T4}$, $R^{T5}$, and $R^{T6}$ is a covalent bond to L;

$R^{T7}$ is alkyl, alkenyl, alkynyl, acyl or aryl; and
$R^{T8}$ is alkoxy or aryl.

15. The binding molecule of claim 11, wherein Z is a doxorubicin derivative of the formula (VI):

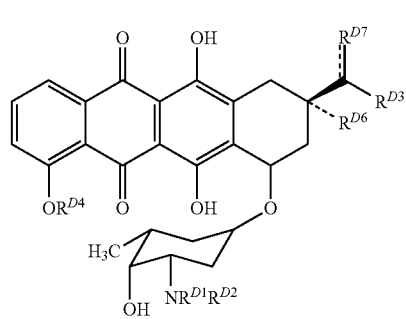

(VI)

wherein:
Y is O or $NR^{D5}$, wherein $R^{D5}$ is alkyl or hydrogen;
$R^{D1}$ and $R^{D2}$ are each hydrogen, or taken together a moiety of the formula (VIa):

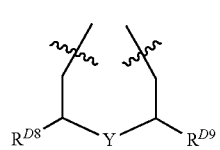

(VIa)

$R^{D3}$ is alkyl;
$R^{D4}$ is alkyl or hydrogen;
$R^{D6}$ is hydroxy or alkyl;
$R^{D7}$ is O or a covalent bond to L;
$R^{D8}$ and $R^{D9}$ are each a covalent bond to L, hydrogen, or alkyl;

provided that one of $R^{D1}$, $R^{D2}$, and $R^{D7}$ is a covalent bond to L.

16. The binding molecule of claim 1, wherein at least one Z is an affinity moiety.

17. The binding molecule of claim 16, wherein said affinity moiety is biotin.

18. The binding molecule of claim 1, wherein at least one Z is a tag moiety.

19. The binding molecule of claim 18, wherein said tag moiety is a fluorescent or radioactive tag.

20. The binding molecule of claim 1, wherein at least one L is cleavable.

21. The binding molecule of claim 20, wherein at least one L is selected such that it is cleaved extracellularly.

22. The binding molecule of claim 20, wherein at least one L is selected such that it is cleaved intracellularly.

23. The binding molecule of claim 20, wherein at least one L is cleaved by a drop of pH, enzymatic cleavage or a change in redox potential.

24. The binding molecule of claim 20, wherein at least one L comprises a disulfide, acetal, ketal, orthoester, ester, trityl, cis-aconityl, thiocarbamoyl, or a peptide moiety.

25. The binding molecule of claim 1, wherein at least one L is of the formula (VII):

$$(CR^{L1}R^{L2})_f\text{—}NR^{L3}\text{—}C(\!=\!O)\text{—}(CR^{L4}R^{L5})_g\text{—}S\text{-}D \quad\quad (VII)$$

wherein $R^{L1}$, $R^{L2}$, $R^{L3}$, $R^{L4}$, and $R^{L5}$ are each independently alkyl, alkenyl, alkynyl, acyl, or hydrogen;

f and g are each independently selected for each occurrence from the group consisting of 0, 1, 2, 3, 4, 5, and 6; and D is a drug attachment moiety.

26. The binding molecule of claim 25, wherein $R^{L1}$, $R^{L2}$, $R^{L3}$, $R^{L4}$, and $R^{L5}$ are each independently hydrogen or methyl.

27. The binding molecule of claim 25, wherein f is 3 and each of $R^{L1}$ and $R^{L2}$ are hydrogen.

28. The binding molecule of claim 25, wherein $R^{L3}$ is hydrogen.

29. The binding molecule of claim 25, wherein D comprises a moiety of the formula (VIII):

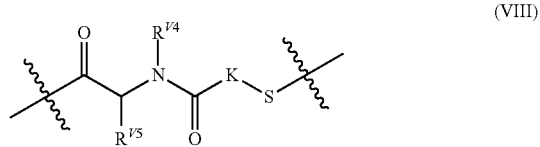

wherein $R^{V4}$ and $R^{V5}$ are each hydrogen or lower alkyl; and

K is an alkyl or cycloalkyl linker comprising 1 to 10 carbon atoms.

30. The binding molecule of claim 25, wherein D comprises a moiety of the formula (IX):

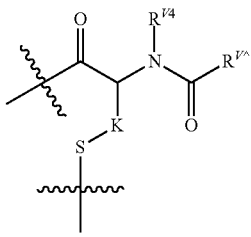

wherein $R^{V4}$ is hydrogen or lower alkyl;

$R^{V6}$ is alkyl comprising 1 to 10 carbon atoms; and

K is an alkyl or cycloalkyl linker comprising 1 to 10 carbon atoms.

31. The binding molecule of claim 29, wherein $R^{V4}$ and $R^{V5}$ are each methyl.

32. The binding molecule of claim 29, wherein K comprises 1, 2, or 3 carbon atoms.

33. The binding molecule of claim 1, wherein the bridging moiety is linked to Ab through a sulfide linkage.

34. The binding molecule of claim 33, wherein B is linked to Ab through an exterior cysteine.

35. The binding molecule of claim 33, wherein B is linked to Ab by cleaving one or more disulfide bonds in Ab.

36. The binding molecule of claim 33, wherein B is linked to Ab without cleaving one or more disulfide bonds in Ab.

37. The binding molecule of claim 1, wherein Ab binds to a molecule preferentially expressed on cancer cells.

38. The binding molecule of claim 1, wherein said Ab binds to CD33.

39. The binding molecule of claim 1, wherein said Ab binds to BR96, IgG, CD56, CD44v6, Her2/neu, Lewis, or CD30.

40. The binding molecule of claim 1, wherein said Ab binds to Cripto.

41. The binding molecule of claim 1, wherein said binding molecule comprises two or more Ab.

42. The binding molecule of claim 41, wherein two or more of said Abs bind to different molecules.

43. The binding molecule of claim 2, wherein said attachment moiety is an amino attachment moiety.

44. The binding molecule of claim 2, wherein said attachment moiety comprises a N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl, or 3-carboxy-4-nitrophenyl moiety.

45. The binding molecule of claim 2, wherein said attachment moiety is a carboxylate attachment moiety.

46. The binding molecule of claim 45, wherein said carboxylate attachment moiety comprises an activated ester or an activated carbonyl moiety.

47. The binding molecule of claim 2, wherein said attachment moiety is a thiol attachment moiety.

48. The binding molecule of claim 47, wherein said thiol attachment moiety comprises an activated acyl moiety, activated alkyl group, a Michael acceptor, or an activated disulfide linkage.-

49. The binding molecule of claim 2, wherein said attachment moiety is of the formula (X):

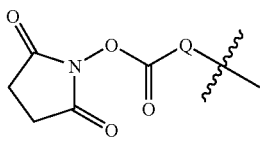

(X)

wherein
Q is a spacer or a covalent bond.

50. The binding molecule of claim 2, wherein said attachment moiety is of the formula (XI):

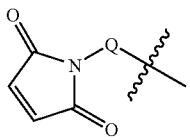

(XI)

wherein
Q is a spacer or a covalent bond.

51. The binding molecule of claim 2, wherein at least one Z is a drug moiety.

52. The binding molecule of claim 51, wherein Z is an anticancer, anti-inflammatory, antibiotic, or anesthetic agent.

53. The binding molecule of claim 2, wherein Z is doxorubicin, eptoside, taxane, paclitaxel, fluorouracyl, mitomycin, camptothecin, a vinca alkaloid, tubulin inhibitor, proteasome inhibitor, epothilone, cephalostatin, gemcitabine, geldanamycin, epothilone, cephalostatin, neocarzinostatin, calicheamicin, maytanisinoids, (RS)-cyclophophamide, 6-mercaptopurin, auristatin E, daunorubicin, or a derivative or analog thereof.

54. The binding molecule of claim 53, wherein Z is a maytansinoid of the formula (IV):

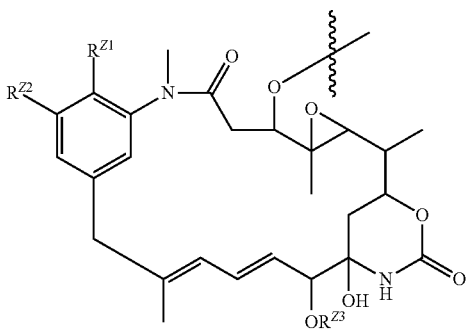

(IV)

wherein
$R^{Z1}$ is halogen or hydrogen; and
$R^{Z2}$ and $R^{Z3}$ are each hydrogen or lower alkyl.

55. The binding molecule of claim 54, wherein $R^{Z1}$ is chlorine and $R^{Z2}$ and $R^{Z3}$ are each methyl.

56. The binding molecule of claim 2, wherein L is cleavable.

57. The binding molecule of claim 56, wherein L is selected such that it is cleaved extracellularly.

58. The binding molecule of claim 56, wherein L is selected such that it is cleaved intracellularly.

59. The binding molecule of claim 2, wherein L is of the formula (VII):

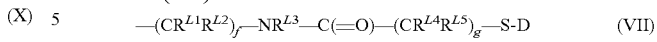

(VII)

wherein
$R^{L1}$, $R^{L2}$, $R^{L3}$, $R^{L4}$, and $R^{L5}$ are each independently alkyl, alkenyl, alkynyl, acyl, or hydrogen;
f and g are each independently selected for each occurrence from the group consisting of 0, 1, 2, 3, 4, 5, and 6; and
D is a drug attachment moiety.

60. The binding molecule of claim 59, wherein D comprises a moiety of the formula (VIII):

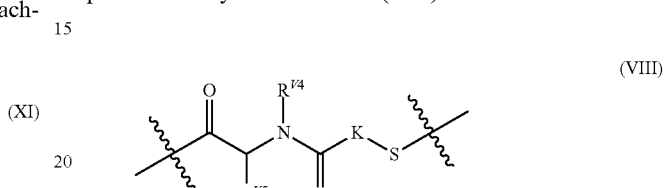

(VIII)

wherein
$R^{V4}$ and $R^{V5}$ are each hydrogen or lower alkyl; and
K is an alkyl or cycloalkyl linker comprising 1 to 10 carbon atoms.

61. The binding molecule of claim 59, wherein D comprises a moiety the formula (IX):

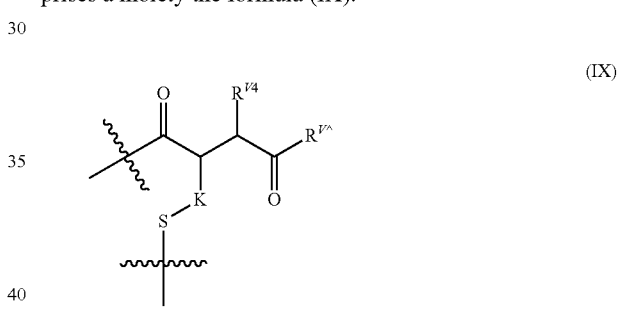

(IX)

wherein
$R^{V4}$ is hydrogen or lower alkyl;
$R^{V6}$ is alkyl comprising 1 to 10 carbon atoms; and
K is an alkyl or cycloalkyl linker comprising 1 to 10 carbon atoms.

62. A method for treating a subject suffering from a disorder that would benefit from treatment with a binding molecule, comprising administering to said subject an effective amount of the binding molecule of claim 1, such that said subject is treated.

63. The method of claim 62, wherein said subject is suffering from cancer.

64. The method of claim 62, wherein said subject is suffering from lymphoma.

65. The method of claim 62, wherein said subject is suffering from an autoimmune disorder or disease.

66. The method of claim 62, wherein said subject is suffering from an inflammatory disease or disorder.

67. A composition, comprising binding molecule of claim 1 and a pharmaceutically acceptable carrier.

68. The composition of claim 67, wherein said pharmaceutically acceptable carrier is suitable for administration parenterally.

* * * * *